(12) United States Patent
Wodnicki

(10) Patent No.: US 7,313,053 B2
(45) Date of Patent: Dec. 25, 2007

(54) METHOD AND APPARATUS FOR CONTROLLING SCANNING OF MOSAIC SENSOR ARRAY

(75) Inventor: Robert Gideon Wodnicki, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 370 days.

(21) Appl. No.: 10/978,012

(22) Filed: Oct. 29, 2004

(65) Prior Publication Data
US 2005/0057284 A1    Mar. 17, 2005

Related U.S. Application Data

(63) Continuation-in-part of application No. 10/248,968, filed on Mar. 6, 2003, now Pat. No. 6,836,159, and a continuation-in-part of application No. 10/383,990, filed on Mar. 6, 2003, now Pat. No. 6,865,140.

(51) Int. Cl.
*H04R 17/00* (2006.01)
*G01S 7/521* (2006.01)

(52) U.S. Cl. ..................................... 367/153; 600/447
(58) Field of Classification Search ................ 367/153; 600/437, 443, 447
See application file for complete search history.

(56) References Cited

U.S. PATENT DOCUMENTS

| | | | |
|---|---|---|---|
| 4,539,564 A * | 9/1985 | Smithson ................ 340/2.26 |
| 4,641,660 A | 2/1987 | Bele | |
| 5,146,435 A | 9/1992 | Bernstein | |
| 5,452,268 A | 9/1995 | Bernstein | |
| 5,490,512 A * | 2/1996 | Kwon et al. ................ 600/447 |
| 5,558,623 A | 9/1996 | Cody | |
| 5,569,968 A | 10/1996 | Lal et al. | |
| 5,596,222 A | 1/1997 | Bernstein | |
| 5,619,476 A | 4/1997 | Haller et al. | |
| 5,684,324 A | 11/1997 | Bernstein | |
| 5,732,706 A | 3/1998 | White et al. | |
| 5,870,351 A | 2/1999 | Ladabaum et al. | |
| 5,894,452 A | 4/1999 | Ladabaum et al. | |

(Continued)

FOREIGN PATENT DOCUMENTS

WO      WO 00/05001      3/2000

OTHER PUBLICATIONS

Ladabaum et al., Surface Micromachined Capacitive Ultrasonic Transducer, IEEE Trans. Ultrasonics, ferroelectrics, and Frequency Control, vol. 45, No. 3, May 1998, pp. 678-690.

(Continued)

*Primary Examiner*—Ian J. Lobo
(74) *Attorney, Agent, or Firm*—Fletcher Yoder

(57) ABSTRACT

A scanning architecture that makes it possible to update only those ultrasonic transducer subelements of a mosaic transducer array that change from view to view. The configuration of the switch matrix is fully programmable. The switch matrix includes access switches that connect subelements to bus lines and matrix switches that connect subelements to subelements. Each subelement has a unit switch cell associated therewith, each unit switch cell comprising at least one access switch, at least one matrix switch, and addressing and control logic. Optionally, each unit switch cell also includes latches for storing the future switch states of the switches to be programmed. The switches themselves have memory for storing their current switch states.

43 Claims, 23 Drawing Sheets

U.S. PATENT DOCUMENTS

| | | | |
|---|---|---|---|
| 5,902,241 | A | 5/1999 | Seyed-Bolorforosh et al. |
| 5,982,709 | A | 11/1999 | Ladabaum et al. |
| 6,004,832 | A | 12/1999 | Haller et al. |
| 6,292,435 | B1 | 9/2001 | Savord et al. |
| 6,320,239 | B1 | 11/2001 | Eccardt et al. |
| 6,325,757 | B1 | 12/2001 | Erikson et al. |
| 6,328,697 | B1 | 12/2001 | Fraser |
| 6,359,367 | B1 | 3/2002 | Sumanaweera et al. |
| 6,381,197 | B1 | 4/2002 | Savord et al. |
| 6,384,516 | B1 | 5/2002 | Fraser |
| 6,443,901 | B1 | 9/2002 | Fraser |
| 6,503,204 | B1 | 1/2003 | Sumanaweera et al. |
| 6,571,445 | B2 | 6/2003 | Ladabaum |
| 6,585,653 | B2 | 7/2003 | Miller |
| 6,589,180 | B2 | 7/2003 | Erikson et al. |
| 6,736,779 | B1 | 5/2004 | Sano et al. |
| 2002/0048219 | A1 | 4/2002 | Ladabaum et al. |

OTHER PUBLICATIONS

Dietz et al., Wideband Annular Array Response, 1978 Ultrasonics Symp. Proc., pp. 206-211.

Bailet et al., A Computer-Controlled Transducer for Real-Time Three-Dimensional Imaging, Acoustical Imaging, vol. 18, Editors: : Lee and Wade, Plenum Press, New York, 1991, pp. 543-551.

Ergun et al., Fabrication and Characterization of 1-Dimensional and 2-Dimensional CMUT Arrays etc., IEEE, 2002, pp. 2361-2367.

Orallean et al., Capacitive Micromachined Ultrsonic Transducers: Next-Generation Arrays for Acoustic Imaging, IEEE Trans. Ultrasonics, Ferroelectronics and Freq. Control, vol. 29, No. 11, Nov. 2002, pp. 1596-1610.

Jin et al., Micromachined Capacitive Ultrasonic Immersion Transducer for Medical Imaging, Proc. 20th Annual Int'l Conf. IEEE Engineering in Medicine and Biology Society, vol. 20, No. 2, 1998, pp. 779-782.

* cited by examiner

METHOD AND APPARATUS FOR CONTROLLING SCANNING OF MOSAIC SENSOR ARRAY

RELATED PATENT APPLICATION

This application is a continuation-in-part of and claims priority from U.S. patent application Ser. No. 10/248,968, now U.S. Pat. No. 6,836,159 and U.S. patent application Ser. No. 10/383,990, now U.S. Pat. No. 6,865,140, both filed on Mar. 6, 2003.

STATEMENT REGARDING FEDERALLY SPONSORED RESEARCH AND DEVELOPMENT

The United States Government may have certain rights in this invention pursuant to U.S. Government Contract Number DAMD17-02-1-0181 awarded by the U.S. Army.

BACKGROUND OF THE INVENTION

This invention generally relates to reconfigurable arrays of sensors (e.g., optical, thermal, pressure, ultrasonic). In particular, the invention relates to a digital scanning architecture for control and configuration of a reconfigurable array of sensors.

Conventional ultrasound imaging systems comprise an array of ultrasonic transducers that are used to transmit an ultrasound beam and then receive the reflected beam from the object being studied. Such scanning comprises a series of measurements in which the focused ultrasonic wave is transmitted, the system switches to receive mode after a short time interval, and the reflected ultrasonic wave is received, beamformed and processed for display. Typically, transmission and reception are focused in the same direction during each measurement to acquire data from a series of points along an acoustic beam or scan line. The receiver is continuously refocused along the scan line as the reflected ultrasonic waves are received.

For ultrasound imaging, the array typically has a multiplicity of transducers arranged in one or more rows and driven with separate voltages in transmit. By selecting the time delay (or phase) and amplitude of the applied voltages, the individual transducers in a given row can be controlled to produce ultrasonic waves that combine to form a net ultrasonic wave that travels along a preferred vector direction and is focused in a selected zone along the beam.

The same principles apply when the transducer probe is employed to receive the reflected sound in a receive mode. The voltages produced at the receiving transducers are summed so that the net signal is indicative of the ultrasound reflected from a single focal zone in the object. As with the transmission mode, this focused reception of the ultrasonic energy is achieved by imparting separate time delay (and/or phase shifts) and gains to the signal from each receiving transducer. The time delays are adjusted with increasing depth of the returned signal to provide dynamic focusing on receive.

The quality or resolution of the image formed is partly a function of the number of transducers that respectively constitute the transmit and receive apertures of the transducer array. Accordingly, to achieve high image quality, a large number of transducers is desirable for both two- and three-dimensional imaging applications. The ultrasound transducers are typically located in a hand-held transducer probe that is connected by a flexible cable to an electronics unit that processes the transducer signals and generates ultrasound images. The transducer probe may carry both ultrasound transmit circuitry and ultrasound receive circuitry.

A reconfigurable ultrasound array is one that allows groups of subelements to be connected together dynamically so that the shape of the resulting element can be made to match the shape of the wave front. This can lead to improved performance and/or reduced channel count. Reconfigurability can be achieved using a switching network.

Recently semiconductor processes have been used to manufacture ultrasonic transducers of a type known as micromachined ultrasonic transducers (MUTs), which may be of the capacitive (MUT) or piezoelectric (PMUT) variety. MUTs are tiny diaphragm-like devices with electrodes that convert the sound vibration of a received ultrasound signal into a modulated capacitance. For transmission the capacitive charge is modulated to vibrate the diaphragm of the device and thereby transmit a sound wave. One advantage of MUTs is that they can be made using semiconductor fabrication processes, such as microfabrication processes grouped under the heading "micromachining". The systems resulting from such micromachining processes are typically referred to as "micromachined electromechanical systems" (MEMS).

The cMUTs are usually hexagonal-shaped structures that have a membrane stretched across them. This membrane is held close to the substrate surface by an applied bias voltage. By applying an oscillatory signal to the already biased cMUT, the membrane can be made to vibrate, thus allowing it to radiate acoustical energy. Likewise, when acoustic waves are incident on the membrane the resulting vibrations can be detected as voltage changes on the cMUT. A cMUT cell is the term used to describe a single one of these hexagonal "drum" structures. The cMUT cells can be very small structures. Typical cell dimensions are 25-50 microns from flat edge to flat edge on the hexagon. The dimensions of the cells are in many ways dictated by the designed acoustical response. It may not be possible to create larger cells that still perform well in terms of frequency response and sensitivity desired.

Unfortunately, it is difficult to produce electronics that would allow individual control over such small cells. While in terms of the acoustical performance of the array as a whole, the small cell size is excellent and leads to great flexibility, control is limited to larger structures. Grouping together multiple cells and connecting them electrically allows one to create a larger subelement, which can have the individual control while maintaining the desired acoustical response. So a subelement is a group of electrically connected cells that cannot be reconfigured. For the purpose of this disclosure, the subelement is the smallest independently controlled acoustical unit. One can form rings or elements by connecting subelements together using a switching network. The elements can be reconfigured by changing the state of the switching network. However, subelements comprise connected cells that are not switchably disconnectable and thus cannot be reconfigured. All of the following analysis is also valid if the array is made of PZT or some other more common or future transducer technology.

Reconfigurability using silicon-based ultrasound transducer subelements was described in U.S. patent application Ser. No. 10/383,990. One form of reconfigurability is the mosaic annular array, also described in that patent application. The mosaic annular array concept involves building annular elements by grouping subelements together using a reconfigurable electronic switching network. The goal is to reduce the number of beamforming channels, while maintaining image quality and improving slice thickness. To reduce system channels, the mosaic annular array makes use of the fact that for an unsteered beam, the delay contours on the surface of the underlying two-dimensional transducer array are circular. In other words, the iso-delay curves are annuli about the center of the beam. The circular symmetry of the delays leads to the obvious grouping of those subelements with common delays and thus the annular array is born. The reconfigurability can be used to step the beam along the larger underlying two-dimensional transducer array in order to form a scan or image. The reconfigurability might also be used to improve performance for multiple transmit applications by assigning more channels to the smaller active aperture in the near field. There are many other applications where reconfigurability might prove useful.

In a mosaic annular transducer array and other mosaic transducer arrays, a large number of ultrasound transducer subelements must be connected together using a distributed switch matrix. The subelements build up larger elements that are used for transmission and reception of ultrasound signals. The configuration of the elements and therefore the subelements changes each time that a new line of data or "view" is acquired. Each time that the configuration changes, the state (on or off) of all of the switches in the switching matrix must be updated to create the required interconnections that build up the new state of the elements and subelements.

There is a need for a digital scanning architecture for controlling and configuring a distributed switching matrix, which architecture has some or all of the following capabilities: (1) efficient programming of the switch cell array such that timing and power constraints are met; (2) the ability to translate aperture patterns from view to view along the axes of the matrix; (3) the ability to configure the array for arbitrary patterns from view to view within time constraints; (4) the ability to change aperture configurations quickly between transmit and receive operations; (5) efficient scaling of the architecture to large tiled arrays in view of power and timing constraints, while retaining flexibility and minimizing complexity of configuration.

BRIEF DESCRIPTION OF THE INVENTION

The invention is directed to reconfigurable arrays of sensors wherein the scanning architecture makes it possible to update only those sensors that change from view to view. The sensors may be optical, thermal or pressure sensors or ultrasonic transducers. The embodiment disclosed herein uses a two-dimensional array of capacitive micro-machined ultrasound transducers (cMUTs) as the underlying grid from which larger elements are constructed. The present invention is not limited, however, to cMUT structures and is equally applicable to other conventional or future transducer technologies.

One aspect of the invention is a device comprising: a multiplicity of sensors arranged along generally parallel lines; a multiplicity of bus lines, a first multiplicity of switches for selectively electrically connecting sensors to bus lines, wherein each switch of the first multiplicity is of a type that can memorize data representing its current switch state, each sensor having at least a respective switch of the first multiplicity associated therewith; a second multiplicity of switches for selectively electrically connecting sensors to each other, wherein each switch of the second multiplicity is of a type that can memorize data representing its current switch state, each sensor having at least a respective switch of the second multiplicity associated therewith; data generator circuitry for generating switch state data representing the state of switches of the first and second multiplicities to be programmed; address generator circuitry for generating address data identifying the switches of the first and second multiplicities to be programmed; and a multiplicity of control logic circuits for outputting switch state control data to the switches of the first and second multiplicities to be programmed in response to receipt of the switch state data, each sensor having a respective control logic circuit associated therewith, the switch state control data controlling the state of the switches and being derived from the switch state data, and each sensor having a respective control logic circuit associated therewith Another aspect of the invention is a device comprising: a multiplicity of sensors arranged along generally parallel lines; a multiplicity of bus lines, and a multiplicity of unit switch cells, each unit switch cell being associated with a respective sensor and comprising: (a) a first switch for connecting the associated sensor to a bus line, (b) a second switch for connecting the associated sensor to a neighboring sensor, and (c) a control logic circuits for outputting switch state control data to the first and second switches in response to receipt of switch state data representing the desired states of the first and second switches, the switch state control data controlling the state of the first and second switches and being derived from the switch state data, and each of the first and second switches being of a type that can memorize data representing its current switch state; data generator circuitry for generating switch state data for selected first and second switches; and address generator circuitry for generating address data identifying which of the first and second switches have been selected to be programmed.

A further aspect of the invention is a device comprising: a multiplicity of sensors arranged along generally parallel lines; a multiplicity of bus lines; a first multiplicity of switches for selectively electrically connecting sensors to bus lines, wherein each switch of the first multiplicity is of a type that can memorize data representing its current switch state, each sensor having at least a respective switch of the first multiplicity associated therewith; a second multiplicity of switches for selectively electrically connecting sensors to each other, wherein each switch of the second multiplicity is of a type that can memorize data representing its current switch state, each sensor having at least a respective switch of the second multiplicity associated therewith; data generator circuitry for generating switch state data representing the state of switches of the first and second multiplicities to be programmed; a multiplicity of latches for storing the switch state data from the data generator circuitry; a multiplicity of data bus lines respectively connected to the sets of latches; means for connecting respective sets of the latches along an X direction to form respective X-direction shift registers; X control means for controlling the shifting of switch state data in an X direction in selected latches; means for connecting respective sets of the latches along a Y direction to form respective Y-direction shift registers; and Y control means for controlling the starting point at which switch state data enters the sets of latches and controlling the shifting of switch state data in a Y direction in selected latches.

Yet another aspect of the invention is a reconfigurable sensor array comprising: a multiplicity of sensors tiled over a two-dimensional area; a multiplicity of bus lines; a multiplicity of switches for connecting selected sensors to each other or connecting selected sensors to respective bus lines, wherein each of the switches comprises respective switch state memory, the switch state memories storing switch state control data representing the current states of the switches; a multiplicity of latches for storing switch state data representing the future states of the switches; and control logic for overwriting the switch state control data in the switch state memories of the switches with new switch state control data derived from the switch state data output from the latches.

A further aspect of the invention is a method for reconfiguring a sensor array comprising a multiplicity of sensors tiled over a two-dimensional area, a multiplicity of bus lines, and a multiplicity of switches for connecting selected sensors to each other or connecting selected sensors to respective bus lines, wherein each of the switches comprises respective switch state memory, the switch state memories storing switch state control data representing the current states of the switches, the method comprising the following steps: (a) generating a first set of address data that identifies a first set of selected switches of the multiplicity to be programmed to achieve a first aperture; (b) generating a first set of switch state data representing future switch states of the first set of selected switches needed to achieve the first aperture; (c) latching the first set of switch state data during a first time period; (d) programming the first set of selected switches with a first set of switch state control data, derived from the first set of switch state data, during a second time period subsequent to the first time period; (e) generating a second set of address data that identifies a second set of selected switches of the multiplicity to be programmed to achieve a second aperture; (f) generating a second set of switch state data representing future switch states of the second set of selected switches needed to achieve the second aperture; (g) latching the second set of switch state data during a third time period subsequent to the second time period; and (h) programming the second set of selected switches with a second set of switch state control data, derived from the second set of switch state data, during a fourth time period subsequent to the third time period.

Other aspects of the invention are disclosed and claimed below.

BRIEF DESCRIPTION OF THE DRAWINGS

Reference will now be made to the drawings in which similar elements in different drawings bear the same reference numerals.

DETAILED DESCRIPTION OF THE INVENTION

The invention is directed to a digital scanning architecture for controlling and configuring a reconfigurable switching matrix. For purposes of illustration, the reconfigurable array will be described with reference to capacitive micromachined ultrasonic transducers (cMUTs). However, it should be understood that the aspects of the invention disclosed herein are not limited in their application to probes employing cMUTs, but rather may also be applied to probes that employ pMUTs or even diced piezoceramic arrays where each of the diced subelements are connected by interconnect means to an underlying switching layer. The same aspects of the invention also have application in reconfigurable arrays of optical, thermal or pressure sensors.

Figure 1:
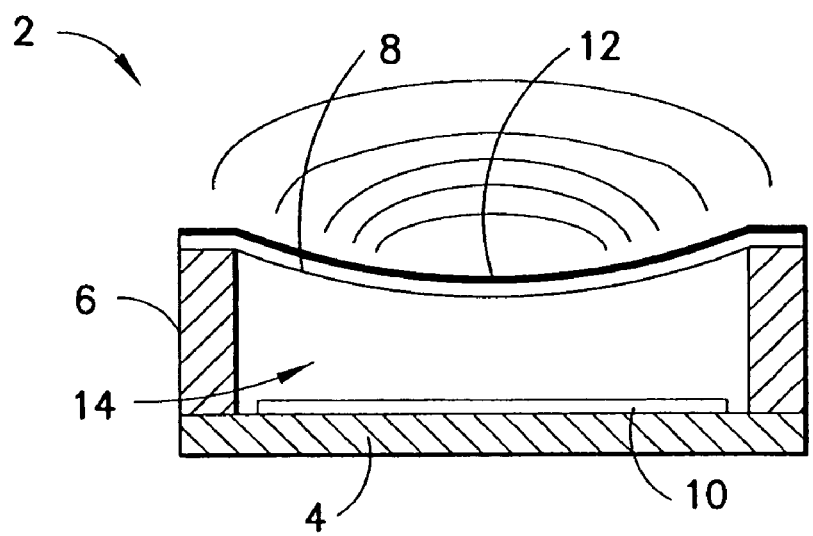
FIG. 1 is a drawing showing a cross-sectional view of a typical cMUT cell.

Referring to FIG. 1, a typical cMUT transducer cell 2 is shown in cross section. An array of such cMUT transducer cells is typically fabricated on a substrate 4, such as a heavily doped silicon (hence, semiconductive) wafer. For each cMUT transducer cell, a thin membrane or diaphragm 8, which may be made of silicon nitride, is suspended above the substrate 4. The membrane 8 is supported on its periphery by an insulating support 6, which may be made of silicon oxide or silicon nitride. The cavity 14 between the membrane 8 and the substrate 4 may be air- or gas-filled or wholly or partially evacuated. Typically, cMUTs are evacuated as completely as the processes allow. A film or layer of conductive material, such as aluminum alloy or other suitable conductive material, forms an electrode 12 on the membrane 8, and another film or layer made of conductive material forms an electrode 10 on the substrate 4. Alternatively, the bottom electrode can be formed by appropriate doping of the semiconductive substrate 4.

The two electrodes 10 and 12, separated by the cavity 14, form a capacitance. When an impinging acoustic signal causes the membrane 8 to vibrate, the variation in the capacitance can be detected using associated electronics (not shown in FIG. 1), thereby transducing the acoustic signal into an electrical signal. Conversely, an AC signal applied to one of the electrodes will modulate the charge on the electrode, which in turn causes a modulation in the capacitive force between the electrodes, the latter causing the diaphragm to move and thereby transmit an acoustic signal.

The individual cells can have round, rectangular, hexagonal, or other peripheral shapes. Hexagonal shapes provide dense packing of the cMUT cells of a transducer subelement. The cMUT cells can have different dimensions so that the transducer subelement will have composite characteristics of the different cell sizes, giving the transducer a broadband characteristic.

Unfortunately, it is difficult to produce electronics that would allow individual control over such small cells. While in terms of the acoustical performance of the array as a whole, the small cell size is excellent and leads to great flexibility, control is limited to larger structures. Grouping together multiple cells and connecting them electrically allows one to create a larger subelement, which can have the individual control while maintaining the desired acoustical response. One can form rings or elements by connecting subelements together using a switching network. The elements can be reconfigured by changing the state of the switching network. However, individual subelements cannot be reconfigured to form different subelements.

MUT cells can be connected together (i.e., without intervening switches) in the micromachining process to form subelements. The term "acoustical subelement" will be used in the following to describe such a cluster. These acoustical subelements will be interconnected by microelectronic switches to form larger elements by placing such switches within the silicon layer or on a different substrate situated directly adjacent to the transducer array. This construction is based on semiconductor processes that can be done with low cost in high volume.

As used herein, the term "acoustical subelement" is a single cell or a group of electrically connected cells that cannot be reconfigured, i.e., the subelement is the smallest independently controlled acoustical unit. The term "subelement" means an acoustical subelement and its associated integrated electronics. An "element" is formed by connecting subelements together using a switching network. The elements can be reconfigured by changing the state of the switching network. At least some of the switches included in the switching network are part of the "associated integrated electronics", as explained in greater detail below.

Figure 2:
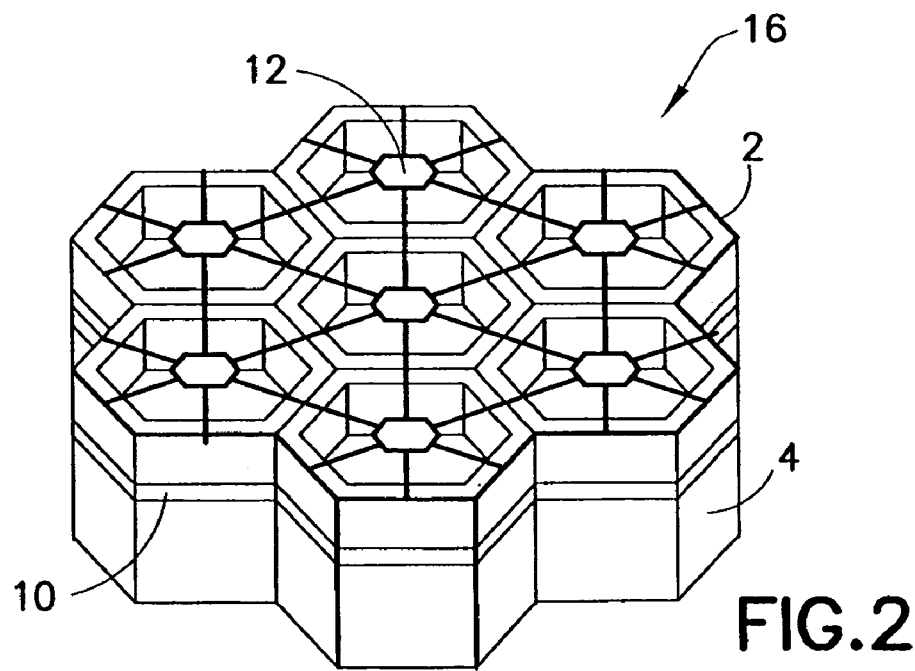
FIG. 2 is a drawing showing a "daisy" subelement formed from seven hexagonal MUT cells having their top and bottom electrodes respectively connected together without intervening switches. This drawing is taken from U.S. patent application Ser. No. 10/383,990.

For the purpose of illustration, FIG. 2 shows a "daisy" transducer subelement 16 made up of seven hexagonal cMUT cells 2: a central cell surrounded by a ring of six cells, each cell in the ring being contiguous with a respective side of the central cell and the adjoining cells in the ring. The top electrodes 12 of each cMUT cell 2 are electrically coupled together by connections that are not switchably disconnectable. In the case of a hexagonal array, six conductors radiate outward from the top electrode 12 and are respectively connected to the top electrodes of the neighboring cMUT cells (except in the case of cells on the periphery, which connect to three, not six, other cells). Similarly, the bottom electrodes 10 of each cell 2 are electrically coupled together by connections that are not switchably disconnectable, forming a seven-times-larger capacitive transducer subelement 16.

Subelements of the type seen in FIG. 2 can be arranged to form a two-dimensional array on a semiconductive (e.g., silicon) substrate. These subelements can be reconfigured to form elements, such as annular rings, using a switching network. Reconfigurability using silicon-based ultrasound transducer subelements was described in U.S. patent application Ser. No. 10/383,990. One form of reconfigurability is the mosaic annular array, also described in that patent application. The mosaic annular array concept involves building annular elements by grouping subelements together using a reconfigurable electronic switching network. The goal is to reduce the number of beamforming channels, while maintaining image quality and improving slice thickness. To reduce system channels, the mosaic annular array makes use of the fact that for an unsteered beam, the delay contours on the surface of the underlying two-dimensional transducer array are circular. In other words, the iso-delay curves are annuli about the center of the beam. The circular symmetry of the delays leads to the obvious grouping of those subelements with common delays lead to the annular array concept. The reconfigurability can be used to step the beam along the larger underlying two-dimensional transducer array in order to form a scan or image.

Figure 3:
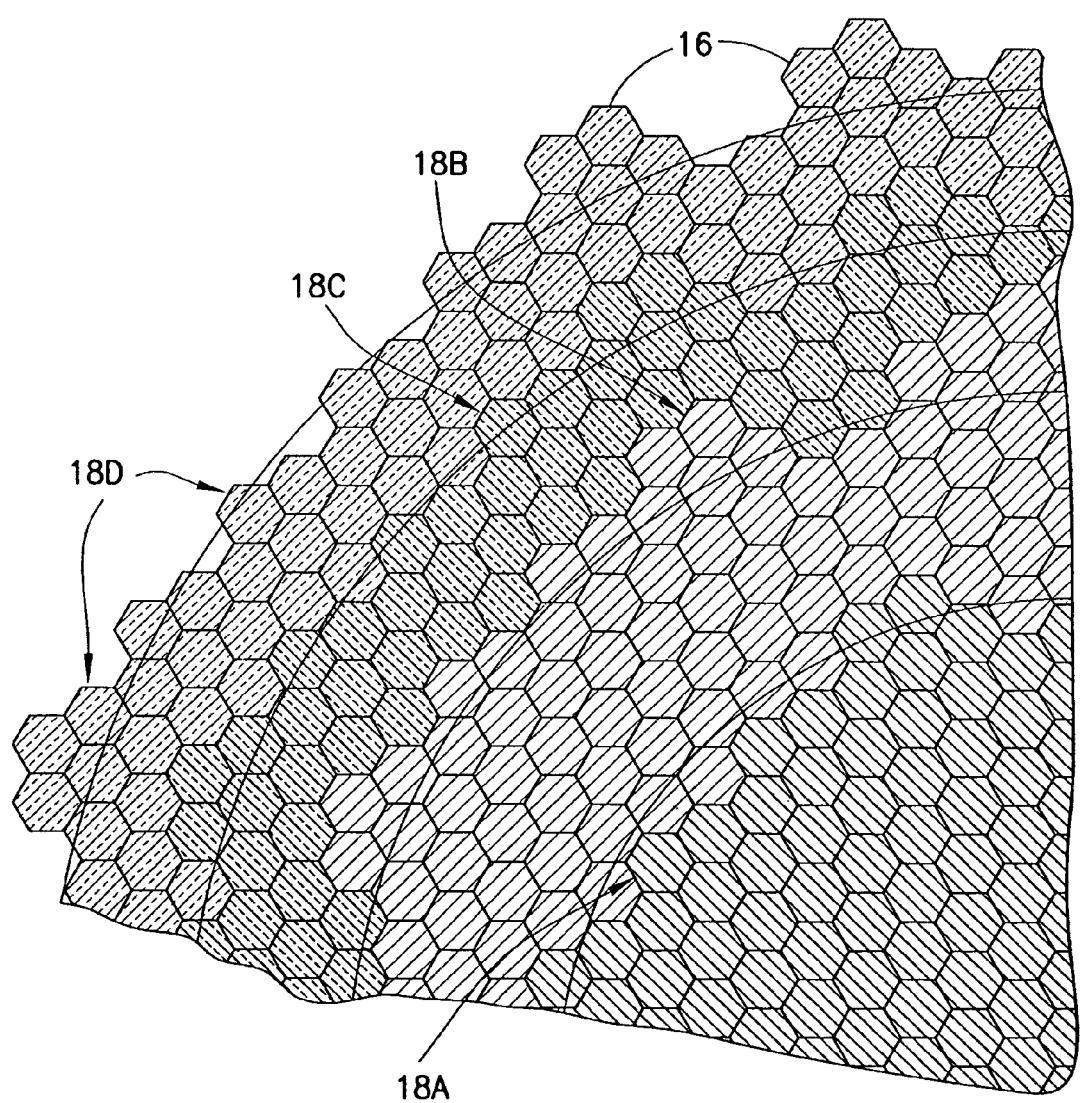
FIG. 3 is a drawing showing a sector of a mosaic array comprising four annular elements as disclosed in U.S. patent application Ser. No. 10/383,990, each element consisting of a tessellation of "daisy" subelements configured to have approximately equal area per element.

There are numerous ways in which one can form transducer arrays using MUT cells and acoustical subelements. FIG. 3 shows one example of tessellations of acoustical subelements to form a mosaic array. In the embodiment shown in FIG. 3, four approximately annular elements (referenced by numerals 18A-D respectively), each comprising a tessellation of "daisy" acoustical subelements (seven MUT cells connected together per subelement), are configured to have approximately equal area per element. The tessellation in each case can be made up of multiple subelement types. The array pattern need not be a tessellation, but can have areas without acoustical subelements. For instance, there could be vias to bring top electrode connections of the acoustical subelement or cells below the array.

The configurations of the invention can be changed to optimize various acoustic parameters such as beamwidth, side lobe level, or depth of focus. Alternatively, the acoustical subelements could be grouped to form one aperture for the transmit operation and immediately switched to another aperture for the receive portion. While FIG. 3 shows respective portions of approximately annular elements, other configurations can be implemented, for example, non-continuous rings, octal rings, or arcs. The choice of pattern will depend on the application needs.

Most apertures will consist of contiguous grouped subelements interconnected to form a single larger element, such as the annular elements shown in FIG. 3. In this case, it is not necessary to connect every subelement directly to its respective bus line. It is sufficient to connect a limited number of subelements within a given group and then connect the remaining subelements to each other. In this way the transmit signal is propagated from the system along the bus lines and into the element along a limited number of access points. From there the signal spreads within the element through local connections.

Figure 4:
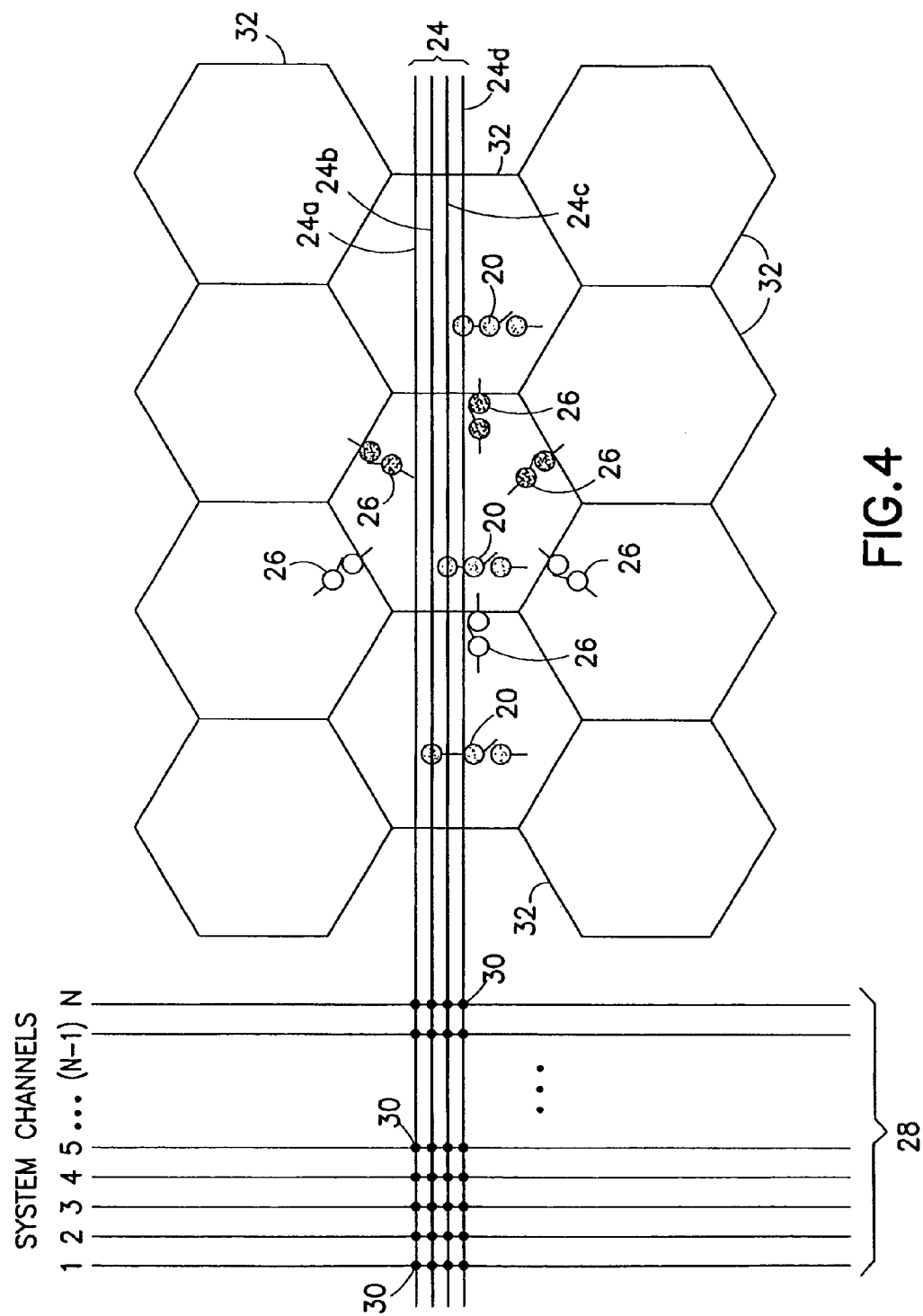
FIG. 4 is a drawing showing an architecture that allows a particular subelement in a particular row of a cMUT array to be connected to any one of a multiplicity of system channel bus lines.

This architecture is illustrated in FIG. 4. Here an access switch 20 is used to connect a given acoustical subelement 32 to a row bus line of bus 24. This architecture is directly applicable to a mosaic annular array. In such a device multiple rings can be formed using the present architecture, wherein each ring is connected to a single system channel using one or more access switches, each of which is connected to a bus line, which is in turn connected to a system channel. The access switches are staggered as shown in FIG. 4 to reduce the number required for a given number of bus lines.

The row bus lines 24 are connected to the system channel bus 28 using a cross-point switching matrix comprising a multiplicity of switches 30, as shown in FIG. 4. A sparse cross-point switching matrix could be used as well in which fewer multiplexer switches 30 would be required. Such an architecture would be more efficient in use of space but would require judicious choice of switch configurations to ensure that all bus lines could be properly connected. It is also possible to dispose both vertically and horizontally running bus lines within an array.

The number of access switches and row bus lines is determined by the size constraints and the application. For the purpose of disclosing one exemplary non-limiting implementation, FIG. 4 shows a single access switch 20 for each acoustical subelement 32 and four row bus lines 24a-24d for each row of the array will be assumed. The second type of switch is a matrix switch 26, which is used to connect a connection point 22 of one subelement (see FIG. 5) to the connection point of a neighboring subelement. This allows an acoustical subelement to be connected to a system channel through the integrated electronics associated with a neighboring acoustical subelement. This also means that an acoustical subelement may be connected to a system channel even though it is not directly connected via an access switch. While FIG. 4 shows three matrix switches 26 per acoustical subelement 32, it is also possible to have fewer than three to conserve area or to allow for switches which have lower on resistance and therefore have larger area. In addition, matrix switches can be used to route around a known bad subelement for a given array. Finally, while hexagonal subelements are shown, rectangular subelements are also possible and these might require fewer switches.

Figure 5:
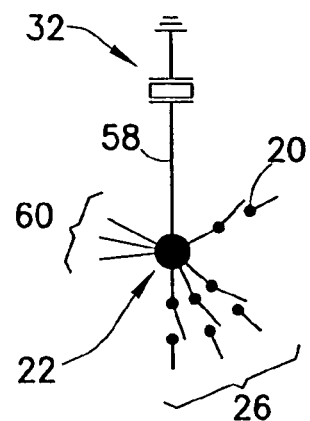
FIG. 5 is a drawing showing connections to a common connection point in the electronics associated with a particular acoustical subelement in the architecture depicted in FIG. 4

Referring to FIG. 5, each of the subelements is connected to a common connection point 22 in the electronics associated with the acoustical subelement 32. This common connection point 22 electrically connects eight components in each subelement. The common connection point 22 connects the acoustic subelement or transducer 32 to the access switch 20 for that subelement via connection 58, to the three matrix switches 26 associated with that subelement, and to the three matrix switches associated with three neighboring subelements via connections 60. A signal that travels through a matrix switch 26 gets connected to the common connection point of the neighboring subelement.

FIG. 4 depicts how the switching network might work for a particular subelement. This is only an exemplary arrangement. A bus 24, which contains four row bus lines 24a through 24d, runs down the row of acoustical subelements 32. FIG. 4 shows only three subelements in this row, but it should be understood that other subelements in this row are not shown. The row bus lines of bus 24 are multiplexed to system channel bus lines of system channel bus 28 at the end of a row by means of multiplexing switches 30, which form a cross-point switching matrix. As seen in FIG. 4, each row bus line 24a-24d can be connected to any one of the system channel bus lines of bus 28 by turning on the appropriate multiplexing switch 30 and turning off the multiplexing switches that connect the particular row bus line to the other system channel bus lines. These multiplexing electronics can be off to the side and thus are not as restricted by size. FIG. 4 shows a fully populated cross-point switch. However, in cases wherein it is not necessary to have switches that allow every bus line to be connected to every system channel, a sparse cross-point switch can be used in which only a small subset of the system channels can be connected to a given bus line, in which case only some of switches 30 depicted in FIG. 4 would be present.

An access switch 20 is so named because it gives a subelement direct access to a bus line. In the exemplary implementation depicted in FIG. 4, there are six other switch connections for each subelement. These connections take the form of matrix switches 26. A matrix switch allows a subelement to be connected to a neighboring subelement. While there are six connections to neighboring subelements for each subelement in this hexagonal pattern, only three switches reside in each subelement while the other three connections are controlled by switches in the neighboring subelements. Thus there is a total of four switches and associated digital logic in each subelement. This is just one exemplary implementation. The number of bus lines, the number of access switches, and the number and topology of the matrix switches could all be different, but the general concept would remain.

Given a particular geometry, the reconfigurable array maps acoustical subelements to system channels. This mapping is designed to provide improved performance. The mapping is done through a switching network, which is ideally placed directly in the substrate upon which the cMUT cells are constructed, but can also be in a different substrate integrated adjacent to the transducer substrate. Since cMUT arrays are built directly on top of a silicon substrate, the switching electronics can be incorporated into that substrate. For a PZT or more conventional implementation, the switch network would simply be fabricated in a separate silicon substrate and attached to the PZT array.

Figure 6:
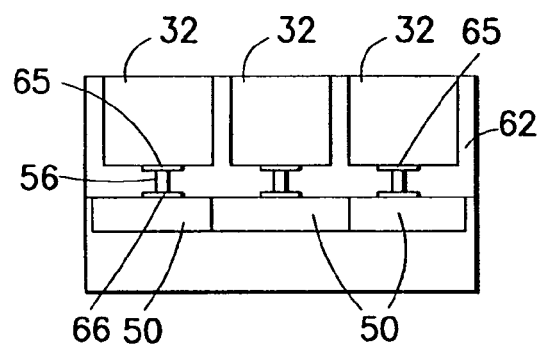
FIG. 6 is a drawing showing a cross-sectional view of a co-integrated cMUT and application specific integrated circuit (ASIC) array.

A cross-sectional view of a co-integrated cMUT and ASIC array is shown in FIG. 6 to illustrate how the connections would be made from the ASIC to the cMUTs. As shown, a single via 56 is used to connect each cMUT subelement 32 to its counterpart CMOS subelement (or "cell") 50. The vias 56, which connect the pads 65 of the signal electrodes to respective conductive pads 66 formed on the switch ASIC, may be embedded in an acoustic backing layer 62.

Figure 7:
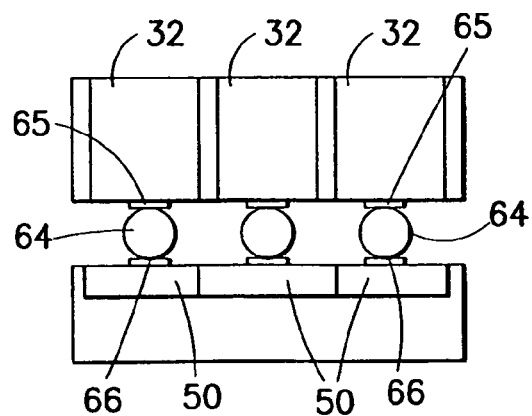
FIG. 7 is a drawing showing a cross-sectional view of a cMUT device substrate connected to an ASIC switch matrix.

It is also possible to build the cMUTs on a separate substrate (e.g., a wafer) and connect them to the ASIC switch matrix separately, as shown in FIG. 7. Here for example, solder bumps 64 and conductive pads 65, 66 are used to connect the individual cMUT subelements 32 to their switch electronics counterparts 50. Other packaging techniques such as Anisotropic Conductive Film (ACF) or flexible interconnect could also be used.

Figure 8:
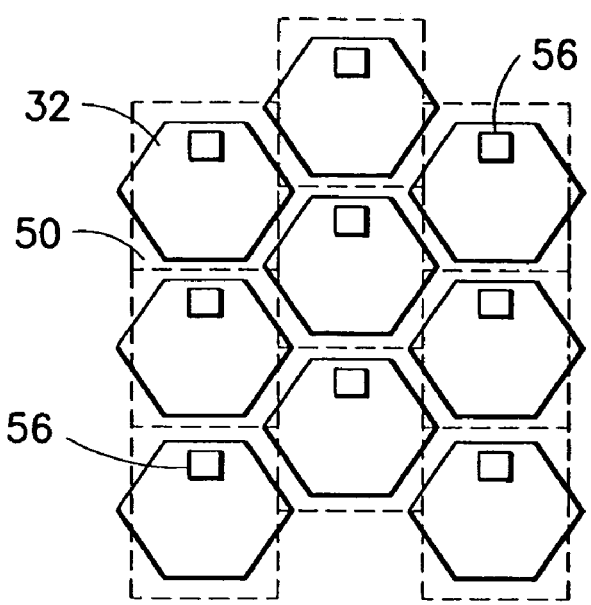
FIG. 8 is a drawing showing a top view of a hexagonal array of cMUT subelements atop associated electronics cells.
Figure 9:
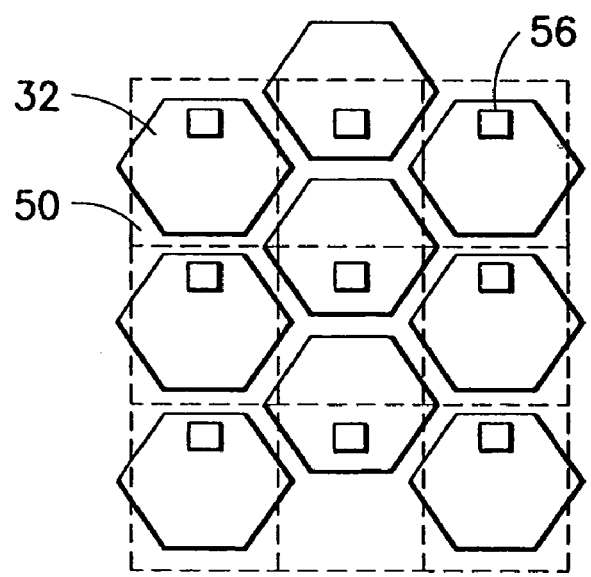
FIG. 9 is a drawing showing a top view of a hexagonal array of cMUT subelements atop a rectangular array of associated electronics cells.

For optimum packing density it is useful to tile the acoustic subelements 32 and the associated electronics cells 50 on a hexagonal grid as illustrated in FIG. 8, which shows a top view of the ASIC switch matrix. Here the CMOS switch cells 50 are disposed in columns where every second column is offset by half a cell height. With proper choice of the cell dimensions, this will yield a perfect hexagonal grid of pads or vias 56 as shown. The vias 56 then contact hexagonal pads on another metal layer (65 in FIG. 6) that forms the basis of connections to the transducer layer above, which is also built on a hexagonal grid. A more straightforward ASIC implementation is illustrated in FIG. 9. Here the CMOS switch cells 50 are arranged on a rectangular grid while the hexagonal acoustical subelements 32 above them are still on a hexagonal grid. As shown the CMOS cell pads or vias 56 still line up correctly to produce the connections such that the CMOS switch cells 50 mate perfectly with the hexagonal acoustical subelements 32. In either case, the hexagonal grid patterns make it possible to realize the mosaic annular array beam patterns as shown in FIG. 3.

Figure 10:
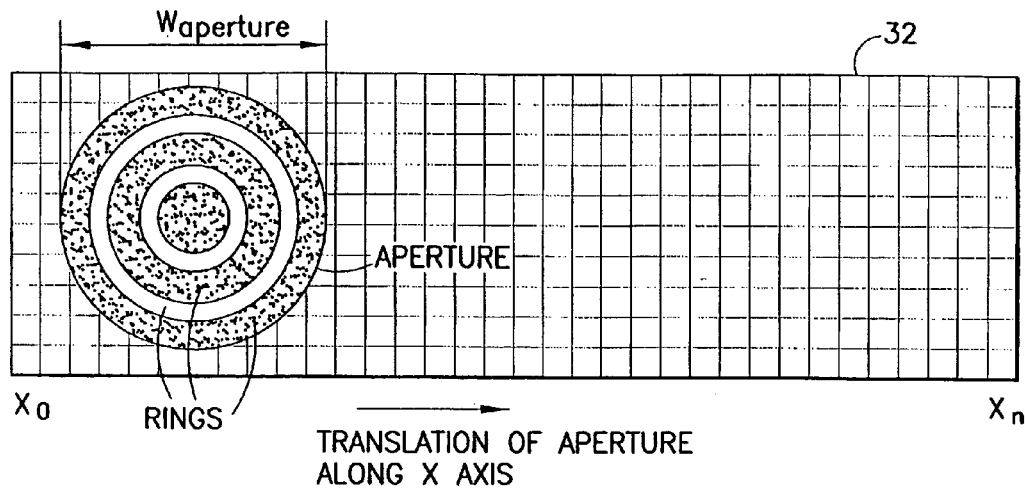
FIG. 10 is a drawing illustrating translation of a ring pattern in the X direction in a mosaic annular array.

In typical operation, the reconfigurable array is programmed with an initial aperture pattern similar to the one shown in FIG. 3. This pattern allows the beamformer to create a beam in front of the array. During imaging, an aperture of width $W_{aperture}$ is scanned across the array as illustrated in FIG. 10. In this way the beam is swept in space in front of the array and the beamformed echoes are used to build up successive lines of the image. The purpose of a reconfigurable array is to be able to accomplish the imaging operation illustrated in FIG. 10 electronically for an arbitrarily complex array pattern. Previous ultrasound scanners are capable of accomplishing electronic scanning but are limited in the complexity of the aperture due to lack of fine distribution of sensor subelements in the elevation direction and fixed geometry.

A fully reconfigurable array as illustrated in FIG. 10 presents a number of significant challenges in implementation. The sensor array is subdivided into tens of thousands of sensor subelements. Beam patterns are built up by grouping the sensor subelements in their connections to a finite number of system transmit/receive and beamforming channels. When used to implement the mosaic annular array concept, the reconfigurable array will form multiple rings that are translated across the array electronically. At each new step in the translation, the entire ring pattern is reprogrammed into the array to create a new configuration. One could also provide the ability to update ring patterns between transmit and receive and at multiple intervals during receive to reduce the distortion of the beam as formed, thereby improving the image quality.

In typical systems, 128 or more beamforming channels are used. Current ultrasound systems use multiplexing architectures that can route the 128 system channels to a fixed number of transducer elements. Using judicious design of these multiplexer networks, it is possible to create a standard scanning pattern with a limited amount of electronics. In most cases however, the scanning pattern is fixed and not reconfigurable due to the limitations of the network. A fully reconfigurable array does not suffer from these limitations; however, it requires a very dense switching matrix to implement it.

In a reconfigurable mosaic transducer array (e.g., the mosaic annular array), the configuration of the elements, and therefore the subelements, changes each time that a new line of data or "view" is acquired. Each time that the configuration changes, the state (on or off) of all of the switches in the switching matrix must be updated to create the required interconnections that build up the new state of the acoustical elements and subelements.

FIG. 10 illustrates this problem schematically. In this example the ultrasound transducer is rectangular, consisting of subelements distributed on a rectangular grid. In a preferred embodiment, the grid is hexagonal, but the rectangular grid is useful for illustration purposes. Also, shown is a transmit aperture pattern consisting of five concentric rings. Each of these rings is built up using the acoustical subelements in the matrix by causing the switches interconnecting the acoustical subelements to be turned on or off. Therefore, before the given pattern can be used to transmit or receive ultrasound signals, it must first be created in the switching matrix by programming the respective on/off states for each of the switches in the array. To illustrate the complexity of this operation, consider that each switch cell could contain four switches, and a nominal aperture consists of 100×100 acoustical subelements. This amounts to 40,000 switches that must be configured before each transmit/receive operation. Obviously, for larger tiled arrays as might be used in a mammography application, the problem grows considerably.

During operation of the array, the aperture must be translated along the axes of the array as is illustrated by the arrow in FIG. 10. This translation is used to acquire different views to build up the lines in the image. Translation may occur along the x axis (as shown) or along the y axis.

Figure 11:
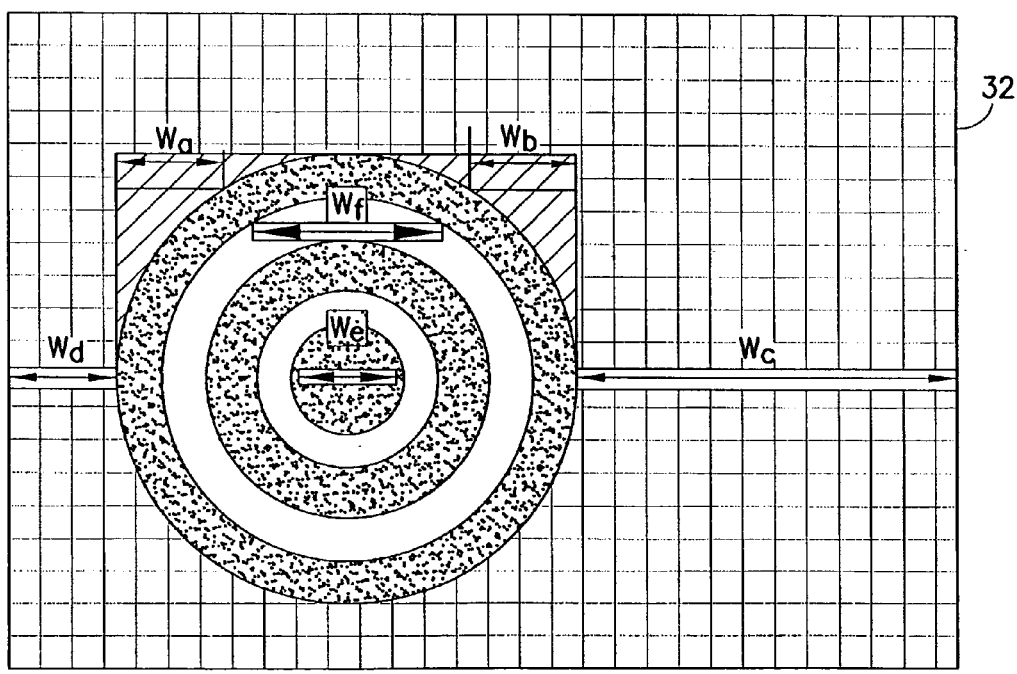
FIG. 11 is a drawing showing unused acoustical subelements for a given translation of the ring pattern shown in FIG. 10.

FIG. 11 illustrates the problem of the large number of unused acoustical subelements in a large array. To translate from the view shown to the next view (not shown), only some of the acoustical subelements in the rings need to be reconfigured. In particular, those acoustical subelements residing in the sections $W_e$ and $W_f$ need not be changed necessarily depending on the type of pattern being used. Also, acoustical subelements in sections $W_a$, $W_b$, $W_c$, and $W_d$ may not have to be changed either. In general, acoustical subelements on the leading and trailing edges of a pattern will change during translation while acoustical subelements internal to the pattern ($W_e$ and $W_f$) and acoustical subelements largely external to the pattern ($W_a$, $W_b$, $W_c$, and $W_d$) will not necessarily change. As can be seen from this example, in an array for which the largest ring is 100 acoustical subelements in diameter while the entire array is 200 acoustical subelements, a significant number of subelements will not need to be changed from view to view. For large tiled arrays the number of unused subelements will be significantly larger. Therefore a means to reconfigure the array such that only the subelements which must change are affected should lead to increased view update times.

In some cases it will be necessary to use a different aperture pattern for transmit and receive operations. This will require either that the array be configurable extremely quickly or that both the transmit and receive states of the array can be programmed together into the array for a given view. The latter technique is advantageous since it allows simultaneous transition for all subelements in the array by changing the state of a single global signal.

In some cases it will be necessary to use different aperture patterns for successive transmit and receive operations which may or may not translate across the array. This would be the case for example during phased array operation, wherein the aperture centroid does not translate but the beam angle is rotated by changing the structure of the rings from view to view.

For very large tiled arrays such as would be used for mammography applications, it is important that the programming time of the array not be limited by the size of the array. For example, a given aperture width and array width ($X_n$ in FIG. 10), it would be detrimental to have to reprogram all of the subelements in the array when translating the aperture pattern in single subelement increments. Additionally, in some cases it should be possible to create and interleave (in time) separate subaperture patterns at different locations in the array. For a large array, this function will be difficult to create if every subelement must be reprogrammed from view to view.

A number of embodiments of the invention will be disclosed hereinafter. These embodiments can be used alone or in conjunction to solve the problem of efficiently scanning a mosaic annular array.

1) Multiplexed Address/Data Scanning Architecture

Figure 12:
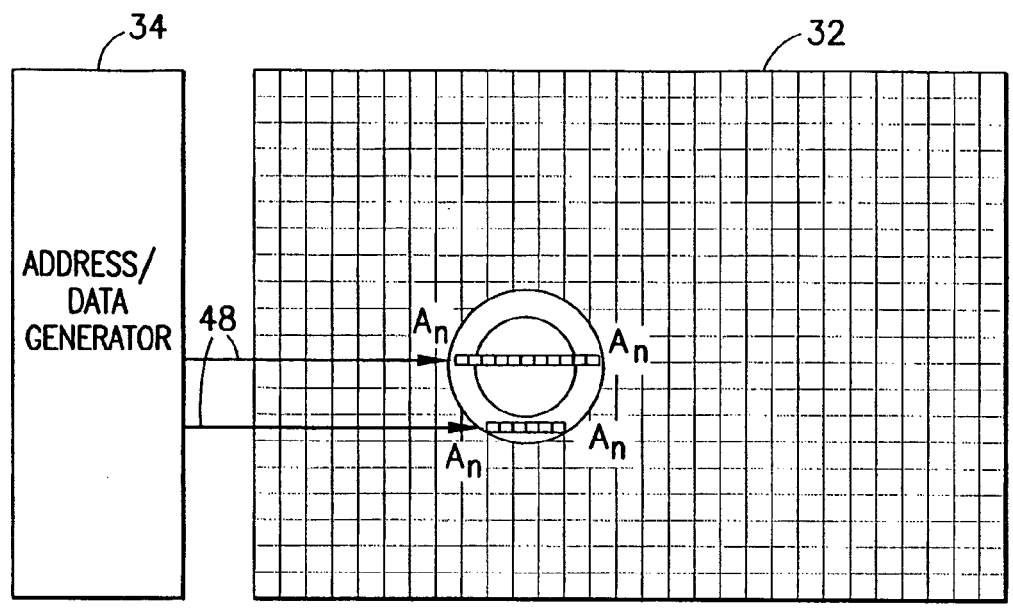
FIG. 12 is a drawing showing a multiplexed address/data type scanning architecture in accordance with one embodiment of the invention.

One embodiment having a multiplexed address/data scanning architecture is illustrated schematically in FIG. 12. In accordance with this architecture, acoustical subelements 32 are grouped in rows (or columns), where all subelements on a given row (or column) share a respective digital address/data bus 48, only two of which are depicted in FIG. 12. Each bus 48 comprises address lines and data lines. Within a given row (or column), each subelement has a unique address on the bus. An address/data generator 34 is contained on chip (or off chip) and transmits data into the array on the shared data bus for each row.

With this arrangement, it is possible to update only those subelements that need to be updated for a given view. In addition, since each row (or column) operates independently, it is possible to update subelements with widely varying x (or y) coordinates simultaneously. This feature would, for example, allow for two simultaneous apertures to be located in opposite corners of the transducer array. In addition, these multiple transmit/receive zones could be made to move independently and in different directions simultaneously.

This multiplexed address/data scanning architecture solves the problem of having to update only the subelements that change from view to view. It also provides the flexibility for arbitrarily different ring patterns from view to view.

A simple variation of this architecture uses separate address and data buses on each row. It requires twice as many digital bus lines but can be operated at twice the data rate.

2) Column-Addressed Scanning Architecture

Figure 13:
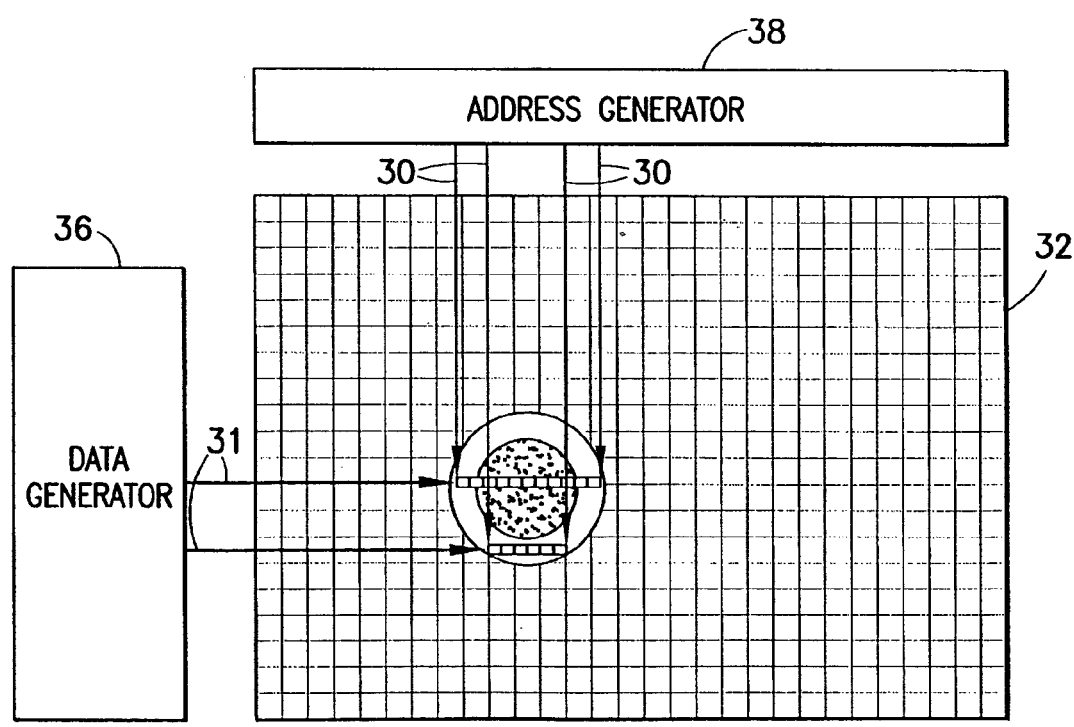
FIG. 13 is a drawing showing a column-addressed type scanning architecture in accordance with another embodiment of the invention.

An embodiment having a column-addressed scanning architecture is illustrated schematically in FIG. 13. This architecture is a useful variant of the multiplexed address/data scanning architecture. The column-addressed scanning architecture operates similarly with the exception that the switch state data is generated by a data generator 36, while addresses are generated by a separate address generator 38 as shown. These addresses are supplied in an orthogonal direction relative to the data, i.e., addresses are supplied via vertical address lines 30, while the data is supplied via horizontal data lines 31. Addresses could be generated using a shift register loaded with a region of interest (ROI) bit pattern that is shifted to move the block of columns that accept the data being input on the row lines. A second shift register would shift a bit in round robin within the ROI bounds to select columns in sequence for the addressing. In this way scanning in the x direction could be accomplished with two shift registers rather than using a shift register in every row, saving a considerable amount of power. The column-addressed scanning architecture also reduces the number of required address lines and simplifies the address circuitry, as will be discussed later.

With this column-addressed arrangement, columns cannot be updated independently; however only those subelements contained within the width of the largest ring need be updated. Therefore, the column-addressed scanning architecture provides a useful compromise for scanning topologies that can be less flexible but require less complicated array electronics. This might be the case, for example, in a high-density array with very small acoustical subelements with not much room for electronics in the array.

3) Multi-Directional Shift Register Scanning Architecture

Figure 14:
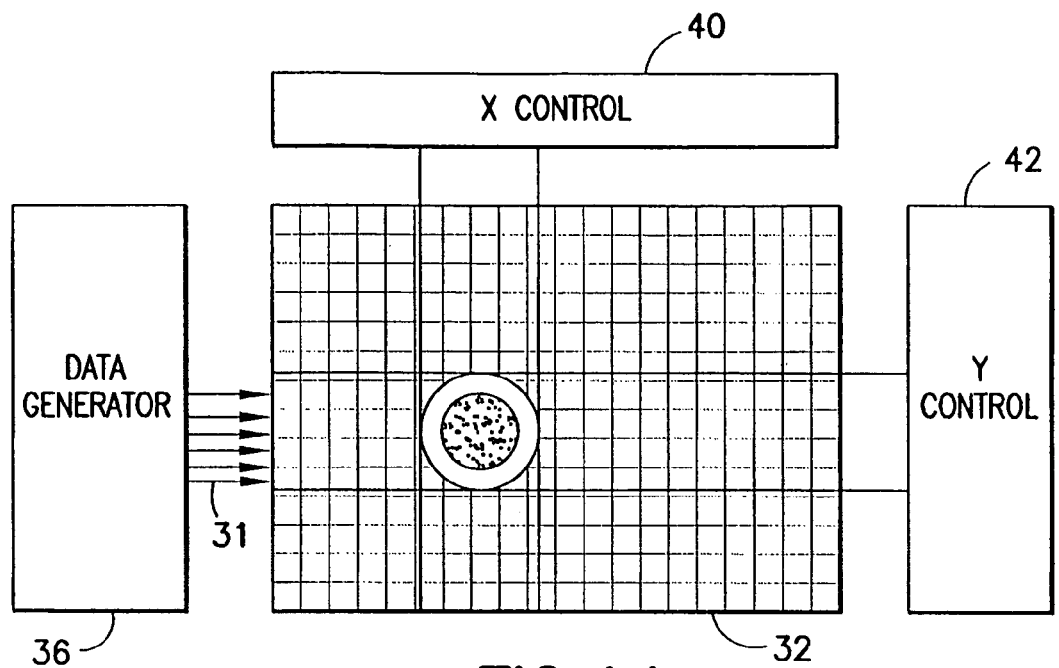
FIG. 14 is a drawing showing a multi-directional shift register type scanning architecture in accordance with yet another embodiment of the invention.

An embodiment having a multi-directional shift register scanning architecture is illustrated schematically in FIG. 14. This architecture is a useful variant of a conventional scanning architecture. In this case data is initially loaded into the array by a data generator 36 one bit at a time and shifted through subsequently to generate successive views. Shifting along the axes of the array (here x and y) is done using control blocks 40 and 42 outside the array that generate control signals to shift the switch state data.

This multi-directional shift register scanning architecture requires similar digital circuitry to implement as the previously discussed architectures, but has the added advantage that the array does not need to be reprogrammed for each view. Translations are effected in a single shift operation rather than by reprogramming the subelements to the next view state. These features yield significant gains in view-to-view translation speed and in power requirements at the expense of flexibility.

With this multi-directional shift register scanning arrangement, it is still possible to create arbitrarily different array patterns from view to view. However, since data originates at the left-hand side of the matrix and must shift through all of the cells on a row to reach the middle, programming time for arbitrary patterns grows linearly with the distance of the transmit aperture from the left-hand side of the array. Therefore, this architecture is useful for a low-power application that does not use large arrays. In addition, large arrays that use sophisticated packaging techniques could be built made up of groups of smaller arrays of this type.

4) Hybrid Scanning Architecture

Figure 15:
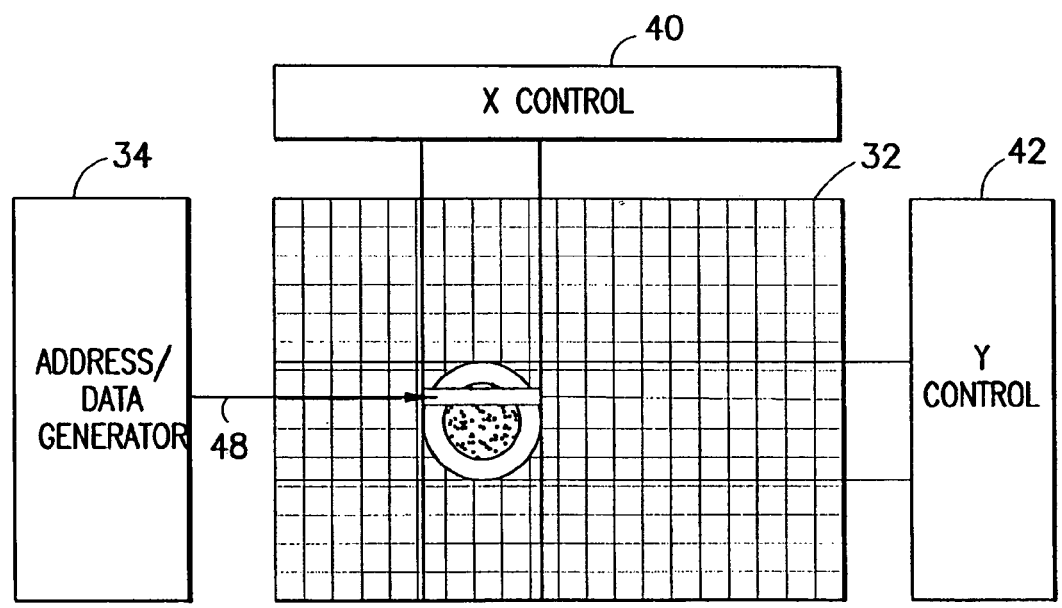
FIG. 15 is a drawing showing a hybrid type scanning architecture in accordance with a further embodiment of the invention.

An embodiment having a hybrid scanning architecture is illustrated schematically in FIG. 15. This architecture combines all of those discussed above in a single flexible arrangement. In this case, data is loaded into the array by an address/data generator 34 using the multiplexed address/data approach. Once it is programmed into the array however, data can be shifted along the axes of the array (here x and y) by means of control blocks 40 and 42, respectively. Therefore, this arrangement can be used in a low-power mode in which a pattern is set up and shifted a single subelement at a time in either the x or y direction. It can also be used in a more flexible mode in which arbitrary patterns need to be built up from view to view, such as in a phased array.

In either case, the advantage of this hybrid arrangement is that there is no requirement to shift through the entire array to program an arbitrary pattern. A region of interest can be programmed and translated independent of all other regions in the array. This allows for low-power operation in applications where patterns shift by a single step from view to view.

An additional important advantage of this hybrid arrangement is the ability to effectively "repair" shift register lines that have inactive elements. This can be accomplished as follows: The initial aperture pattern is programmed into the array. Subsequent to that, each time a shift occurs, shift register cells that are inoperable, as well as those that take their inputs from inoperable cells, are updated using a multiplexed address/data bus 48. Since the number of such inoperable cells is relatively small, the "repair" operation will take only a fraction of the time of updating the entire array, and will also require very little power.

In a useful variant of this hybrid architecture, the x control block 40 can be used to control the starting point at which data enters the shift registers in the array. In this case row address lines are not used, while row data lines are still run across the array. The data lines are used to bypass those shift register elements that would normally have to be used in the traditional shift register arrangement. This arrangement gives up the flexibility of uniquely determining the cells to be programmed, but requires somewhat less circuitry to implement.

Each of the scanning architectures described above is essentially composed of two parts: an array of switch cells (one for each acoustical subelement 32 in the mosaic transducer array) that are largely similar, and scanning circuitry integrated outside of the array. In the following sections the details and operation of these circuits are described for some of the architectures discussed above.

A) Scan Circuitry Architectures

1) Multiplexed Address/Data Type Scanning Architecture

Figure 16:
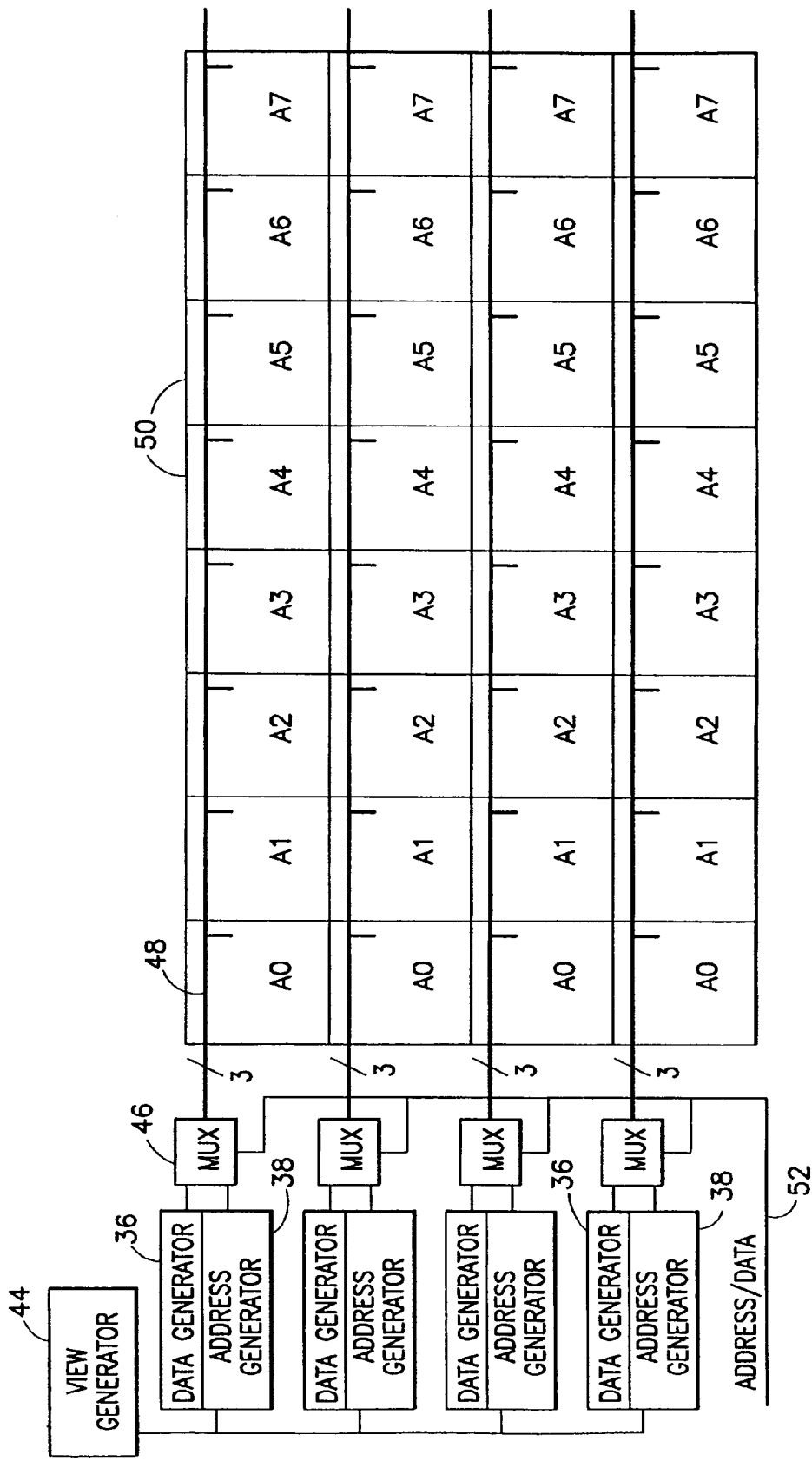
FIG. 16 is a functional illustration of the multiplexed address/data type scanning architecture shown in FIG. 12.

The multiplexed address/data bus type scanning architecture for programming of digital data into the unit switch cells 50 is illustrated in FIG. 16. Every column of cells 50 has a unique address as shown (A0, A1, . . . A7). In this example, only eight columns are shown; however, the device could potentially contain hundreds of columns. Every row of cells 50 shares a multiplexed address/data bus 48. In addition, each row has a dedicated address/data generator 34 that programs the respective bus 48 via a respective multiplexer 46. In this way, all rows are programmed in parallel.

The data and address generator 34 for each row could be located on the chip outside of the array. They may also be located off-chip in a field-programmable gate array (FPGA), digital application-specific integrated circuit (ASIC) or central processing unit (CPU) or combination of these. The programming operation is controlled by a view generator 44, which receives input from the ultrasound imaging system requesting a specific next state array configuration. The view generator 44 then programs the data and address generators 34 to configure the array as required for the given view. The view generator may also be implemented as an FPGA, a digital ASIC, a CPU, or a combination thereof, and may contain, SRAM, DRAM, ROM, EPROM, EEPROM, MRAM or other memory storage technology for local storage of configuration data. Configuration data may also be calculated during operation algorithmically, based on calibration data, aperture scanning information, inputs by the operator and default calibration data as needed.

The data and address generators 34 could be implemented in random access memory (RAM) or other memory storage technology as lookup tables. Given the view number in a sequence of views, a respective block of each RAM would be read out, where the contents of the RAM contains a series of pairs of n bit numbers, with the first number being the address of the cell in the row and the second number being the switch state data to be written to that cell. The operation could also be done algorithmically, where the data for a given cell is determined on the fly as cells are updated.

In the example shown in FIG. 16, data is written to the eight cells 50 on a 3-bit bus 48 (in the case of 16 cells in a row, a 4-bit bus would be used, and so forth). The first word in the write sequence is the 4-bit address of the column to which the data is going. The next word consists of 4 bits, wherein each bit determines the future state of one of the switches in the given switch cell 50. The address is output by the address generator to one input of a multiplexer 46, while the switch state data is output by the data generator to another input of the multiplexer 46, with the state of the multiplexer being determined by whether an ADDRESS or DATA multiplexer state control signal is input to the multiplexer on line 52.

Still referring to FIG. 16, data writes can proceed from left to right in sequence beginning with column 0, or from right to left beginning with column 7. They could also be arbitrary and independent as is best suited for the data to be programmed. For example, row 1 might program cells A0 and A5, at the same time that row 2 programs cells A3 and A4. This feature will be useful for quickly setting up an arbitrary pattern.

Figure 35:
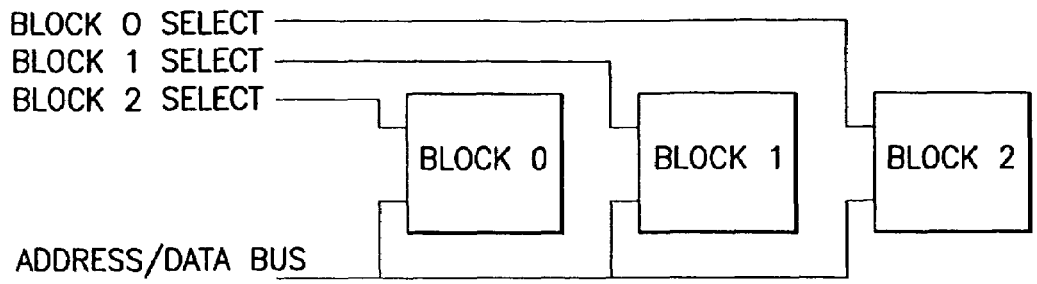
FIGS. 35-37 are drawings showing respective embodiments of block address controllers.
Figure 36:
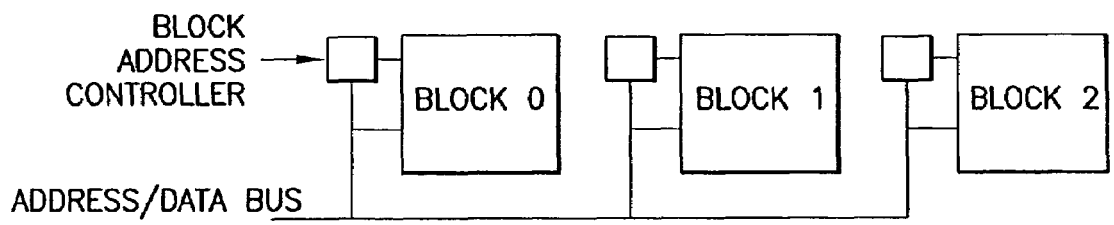

While the address bus could be larger than the 3 bits shown, block addressing is also possible with this scheme. Banks of cells would be selected for 3-bit addressing successively either by an external address generator integrated along the columns (as shown in FIG. 35), or by writing data to block address controllers integrated inside of the array at block increments (as shown in FIG. 36). For example, in a large matrix array as would be used in mammography, block addressing could be done in sections of 32 or 64 requiring 5 or 6 address lines, while the entire array might have as many as 40 such blocks.

Figure 37:
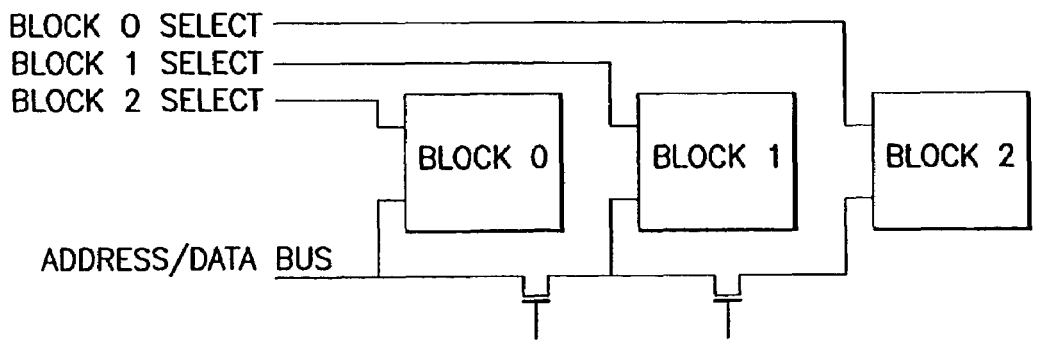

In an alternate embodiment, digital bus lines can be broken into banks of columns with each bank separated by a MOSFET switch, as shown in FIG. 37. The address circuitry would be configured to select successive banks as addressing moves from left to right within the array. This technique reduces the amount of capacitive loading on the line drivers for a significant portion of the addressing cycle and therefore saves power over the original architecture.

2) Column-Addressed Scanning Architecture

Figure 17:
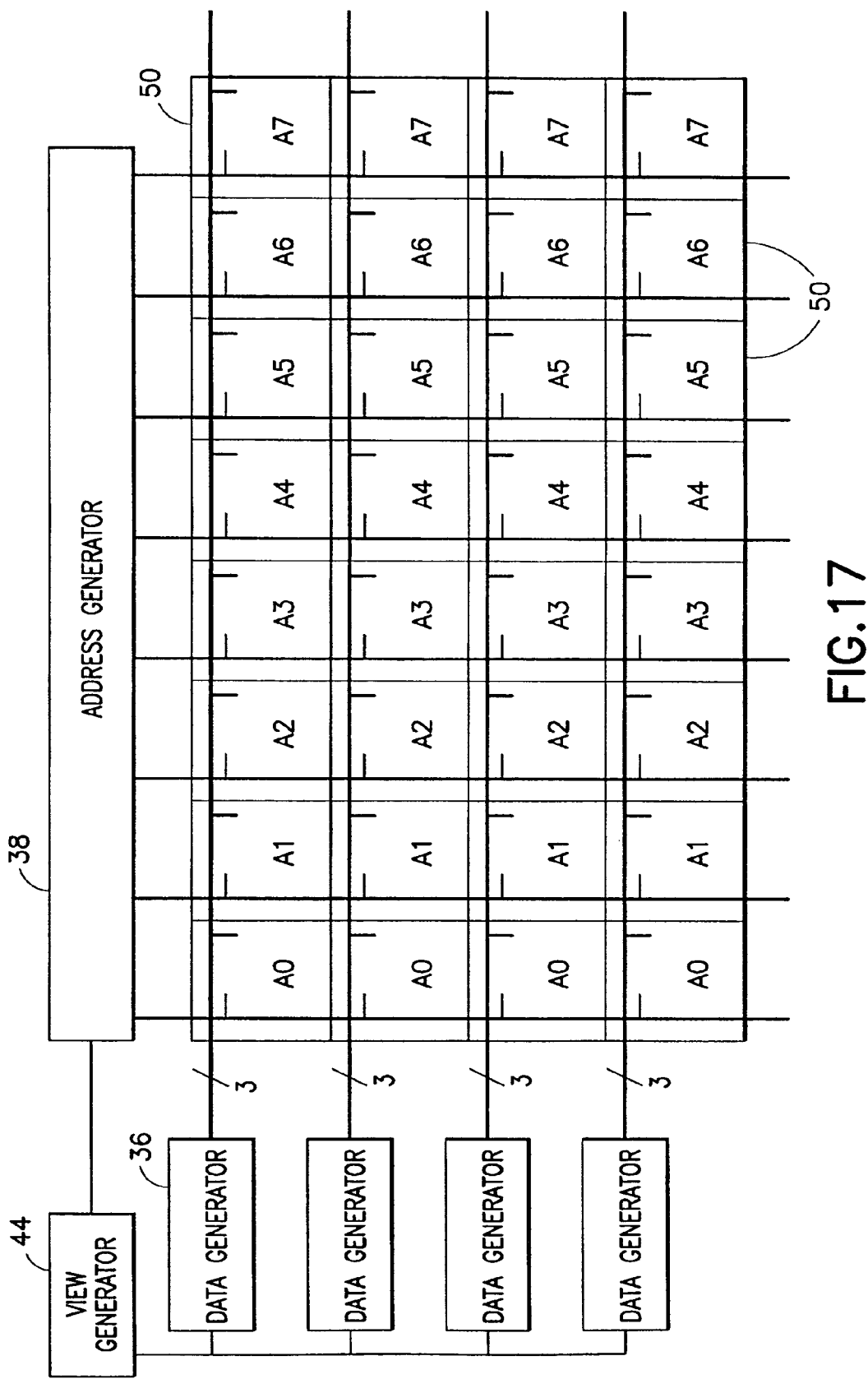
FIG. 17 is a functional illustration of the column-addressed type scanning architecture shown in FIG. 13.

The column-addressed scanning architecture for programming of digital data into the unit switch cells 50 is illustrated in FIG. 17. This scheme is similar to multiplexed addressing in that data generators 36 are located at each row of the device. In this case, however, a single address generator 38 is shared by all rows as shown. A region of interest is created by the address generator 38 such that only columns containing cells which must be updated are selected. Addressing proceeds incrementally from left to right beginning at the first column that contains cells to be updated and ending with the last column that contains cells to be updated.

This scheme has the advantage of less complexity within the array, but does not benefit from full flexibility in programming. This is because changing the view requires that all cells within the aperture ring pattern need to be updated by default. So for example, if only the cells on row 4 need to be updated, all of the cells in all rows will be updated at the same time, requiring more power to execute. Also, if cells in opposite corners of the array need to be updated, the entire array must be scanned through. A slight modification would be to use multiple independent Region of Interest (ROI) shift controllers (i.e., scanners) to allow for handling independent and distantly spaced apertures in the same large array. These multiple ROIs could be created using two separate and independent shift registers for the X-controller, or could also be done using two separate decoders with the addresses being written to these to select which signal lines to turn on.

Figure 38:
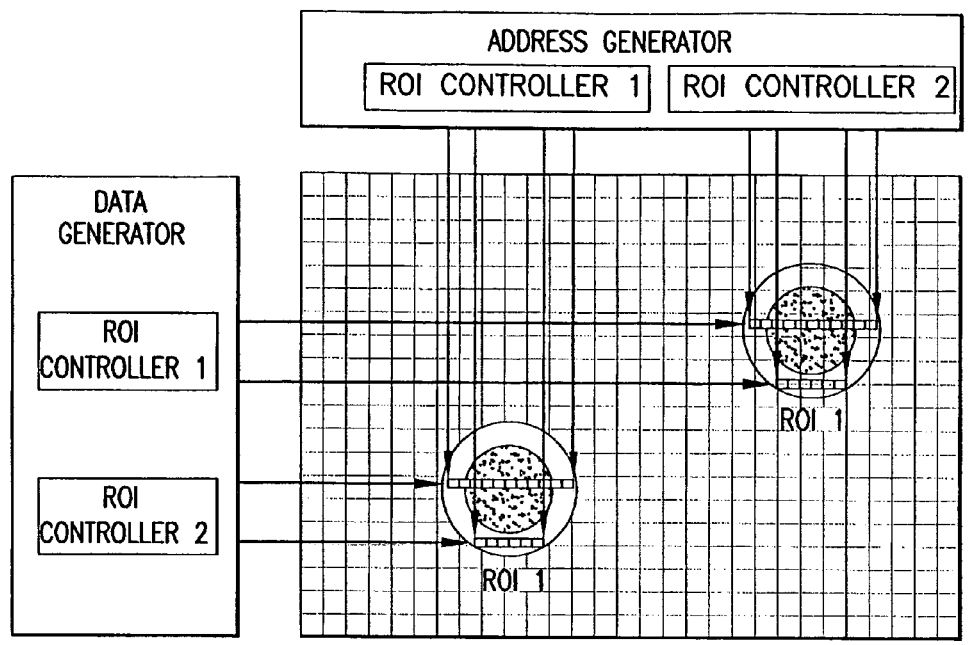
FIG. 38 is a drawing showing the concept of multiple region of interest shift controllers.

FIG. 38 illustrates the concept of multiple region of interest (ROI) shift controllers. Here data is actually written to two completely independent apertures simultaneously in different parts of the array. This technique allows for multiple scan beams to be created using a single array. The two (or more) independent apertures are controlled using two (or more) independent ROI controllers (only two are shown). The ROI shift controllers set the extent of the apertures in the X and Y directions and control independent data transfer to the cells specified by these apertures.

3) Alternate Embodiment of Multiplexed Address/Data Scanning Architecture

Figure 18:
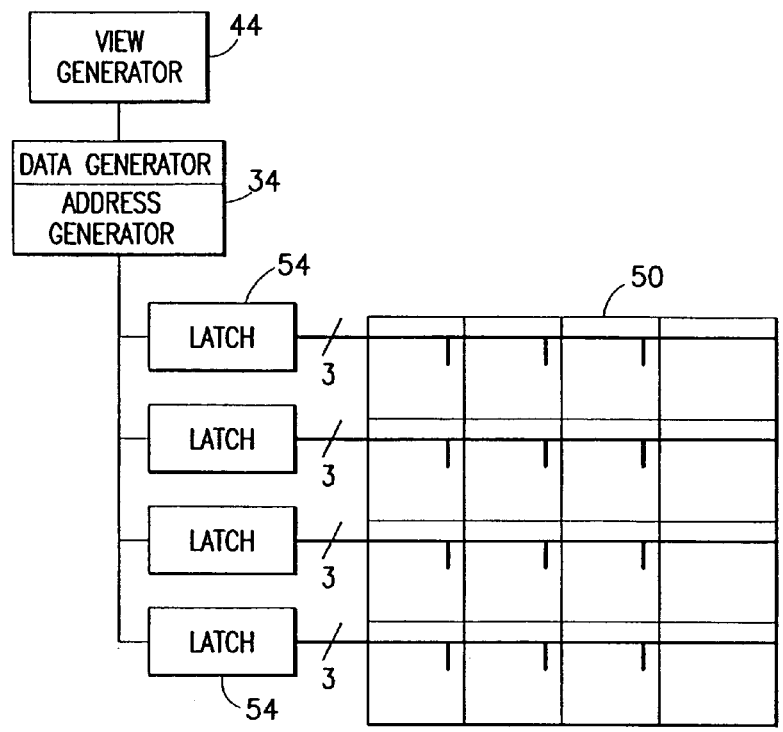
FIGS. 18 and 19 are drawings showing respective alternative embodiments of the multiplexed address/data type scanning architecture.

An alternate form of the multiplexed address/data bus type scanning architecture for programming of digital data into the unit switch cells 50 is illustrated in FIG. 18. This scheme differs from the original in that unique address and data generators are not provided for every row. Instead these are replaced by a single address/data generator 34 combined with a series of latches 54 to store the data in a scanned addressing operation. In one embodiment, the generator is off-chip while the latches are on-chip. This greatly reduces the routing of signals on-chip, but comes at the expense of lower scanning speeds due to the serial update of the row data, To update a unit switch cell 50, the row address is first read out. This is used to select the latch on the given row, which is then written with the column address of the unit switch cell. This address is then used to select the unit switch cells for the data write. Similarly, the data is read out from the data generator and transferred first through the latch 54 and then on into the addressed unit switch cell. To update a large number of unit switch cells, multiple latches could be set up at each step and used to update respective cells simultaneously.

Figure 19:
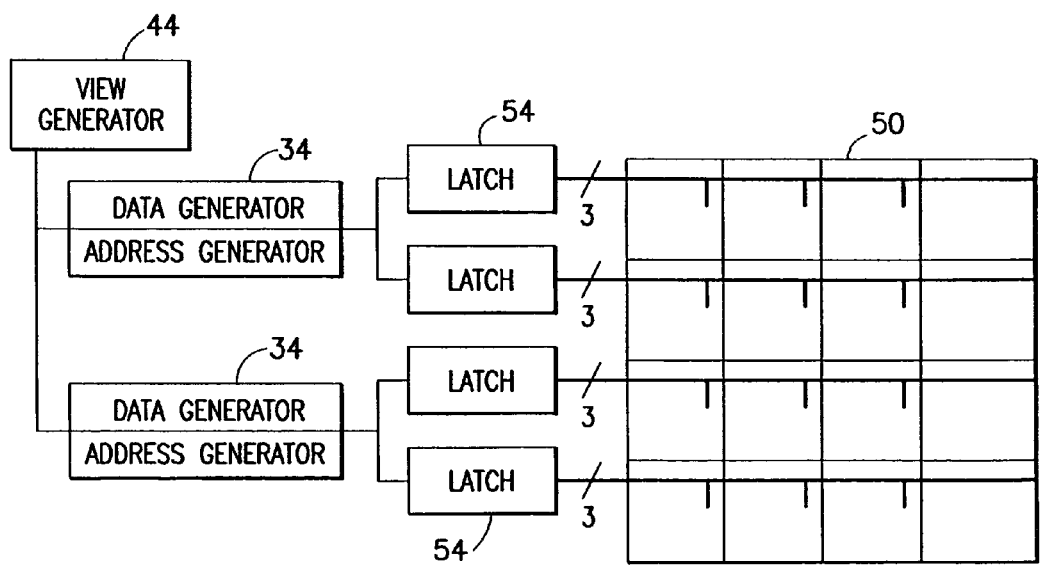

FIG. 18 shows how this scheme could be used with just a single address/data generator 34, while FIG. 19 shows how multiple address/data generators could be used. In the latter case, significantly fewer generators would be used than the original multiplexed addressing embodiment, however, the update time would be faster than for the scheme of FIG. 18. For example, in a system with 100 rows and 10 generators, the scheme of FIG. 19 uses 10 times fewer generators than the scheme shown in FIG. 16, but updates 10 times faster than the scheme shown in FIG. 18.

Both forms of this embodiment have the added advantage of requiring less logic integrated next to the array for implementation, but require longer times to effect a view configuration. For a large array in which aperture patterns are relatively square (circular) and constitute a small fraction of the total array area, this scheme provides significant advantages in terms of power and logic array requirements.

4) Hexagonal Array Routing

Figure 20:
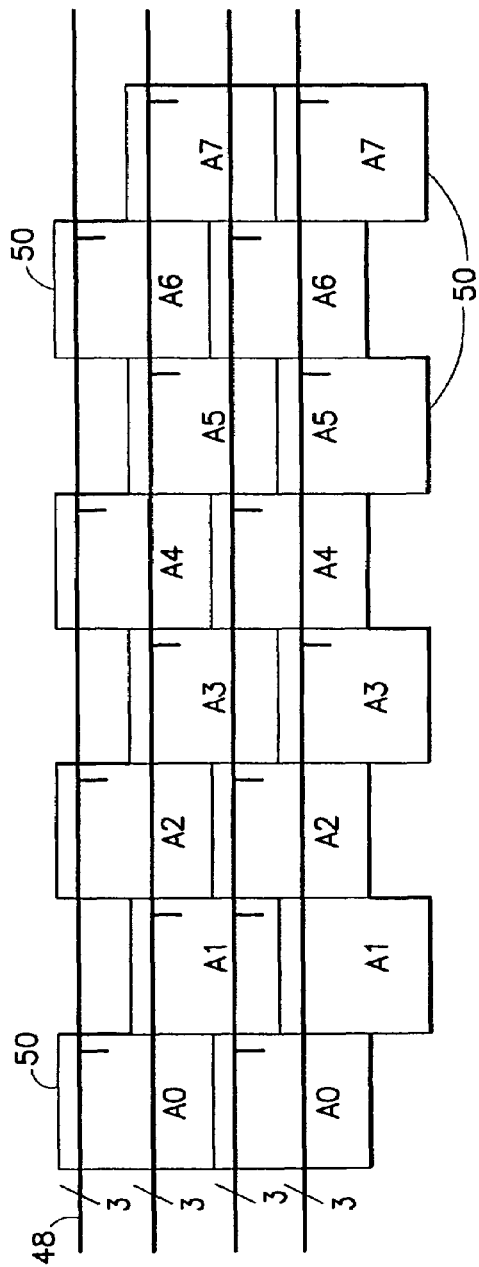
FIGS. 20 and 21 are drawings showing respective alternative embodiments of hexagonal addressing for a mosaic annular array.
Figure 21:
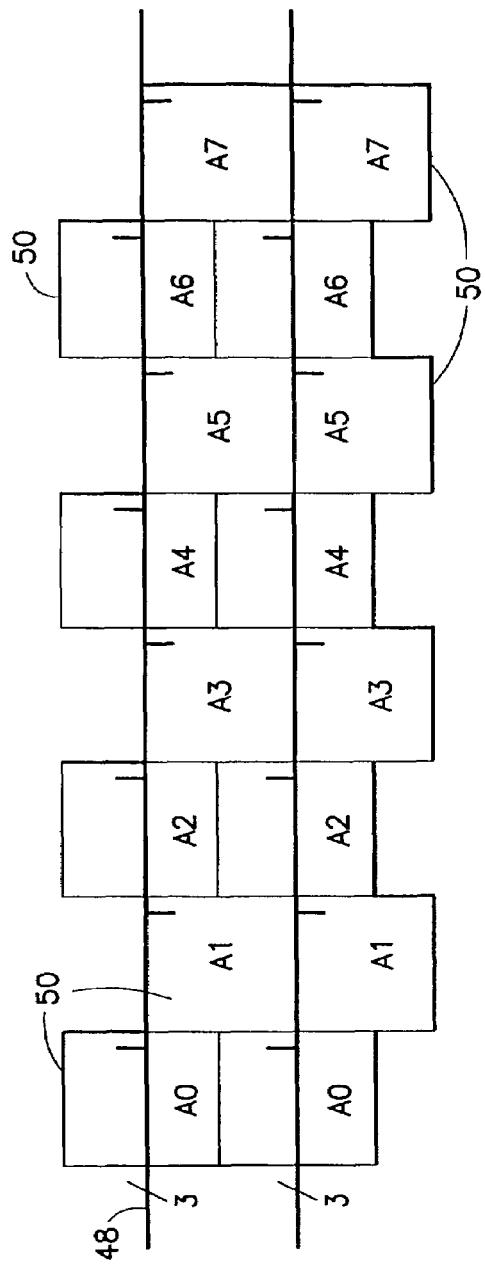

The architectures described above are readily implemented in the case of a hexagonal subelement array. FIGS. 20 and 21 show two alternative embodiments for routing of bus lines 48 in such a hexagonal array of unit switch cells 50. The embodiment shown in FIG. 20 requires more bus lines 48 but allows all unit switch cells 50 to be identical, which is advantageous for ASIC layout purposes. The embodiment shown in FIG. 21 requires half as many bus lines, but alternates cell types and therefore is incrementally more complicated to implement.

5) Multi-Scanning Architecture

While all of the architectures discussed above show column or row scanning circuitry on one side of the array, it is also advantageous to provide scanning circuitry on both sides of the array for the same operation (not shown in the drawings). This is done, for example, on a row basis by dividing the row into left and right segments with a break in the middle of the array. The advantage of this arrangement is that it reduces the requirements on the line drivers that drive the digital lines on the row. This arrangement also doubles the write speed of the configuration since now the two halves of the array can be updated simultaneously.

This technique can also be applied to the column address lines by dividing the array into top and bottom halves. In this case, driver requirements are reduced, and top and bottom halves of the array can be updated independently and simultaneously also.

In accordance with an alternative embodiment of the architectures discussed above, the address and data bus could be separate, which would decrease the write time at the expense of more area used for routing.

In accordance with yet another alternative embodiment, each row could contain two distinct multiplexed address/data buses, wherein the first bus addresses even blocks of 32 or more cells and the second bus addresses odd blocks of 32 or more cells. This scheme would again increase the write time by a factor of two.

6) Translation in Y Direction

Translation of the subaperture pattern in the Y direction can be done by any of the following means: (1) algorithmically, by translating the pattern in the data generator RAM or data generator algorithm; (2) by changing the start address of the y latch to write to when using the single generator model; (3) by using address/data generators in both the x and y directions; and (4) by using the shift register model in which Y controllers are used to shift data in the Y direction.

B) Array Cell Architectures

In accordance with various embodiments of the present invention, each of the unit switch cells in the mosaic transducer array comprises analog switches along with associated logic for programming the states of the switches. As disclosed in U.S. patent application Ser. No. 10/248,968 entitled "Integrated High-Voltage Switching Circuit for Ultrasound Transducer Array", the switch architecture is such that the switches themselves have memory. For this reason, some of the architectures described below do not require digital memory cells. The addition of digital memory in the form of latches is useful in that it implements the requirement for fast transition of aperture patterns between successive transmit and receive operations. While the switch architecture discussed in U.S. patent application Ser. No. 10/248,968 uses high-voltage DMOS transistors, the scanning architecture discussed here is entirely amenable to alternate switch devices, including (but not limited to) low-voltage CMOS or MOS switches and high-voltage MEMS-based switches. While not all of these alternative switches contain their own internal memory, secondary latches can be added in their control circuitry to make possible the architectures described herein.

1) State Memory Latches

For a mosaic transducer array with one access switch and three matrix switches per subelement, four latches are required to hold the future state of the switches. These latches should be capable of being written to as well as read so that they can be tested.

FIGS. 22 through 25 show alternate embodiments of the logic contained within each latch for this architecture. Each latch outputs two switch state control signals N and P to a switch control circuit (not shown) that either turns on or turns off a respective switch, such as the switches disclosed in U.S. patent application Ser. No. 10/248,968. For example, a predetermined change in the level of the control signal P would cause the switch to be turned on, while a predetermined change in the level of the control signal N would cause the switch to be turned off.

Figure 23:
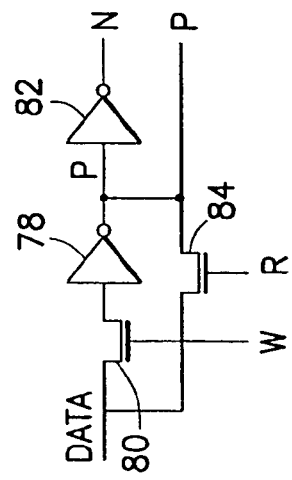
FIGS. 22 through 24 are drawings showing respective embodiments of a latch incorporated in each unit switch cell in accordance with respective embodiments of the invention.
Figure 22:
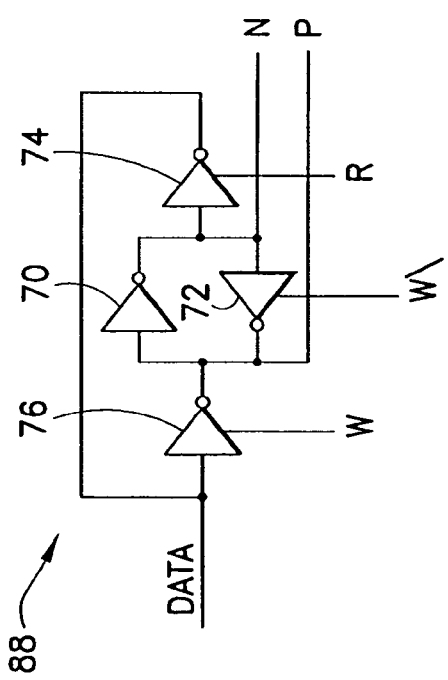
Figure 25:
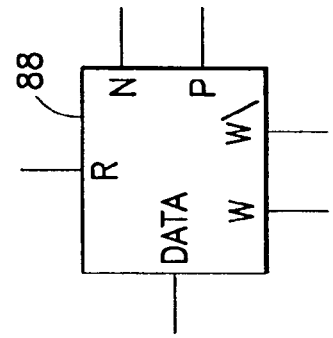
FIG. 25 is a high-level block diagram of the latch of FIG. 22 showing its input and output signals.
Figure 24:
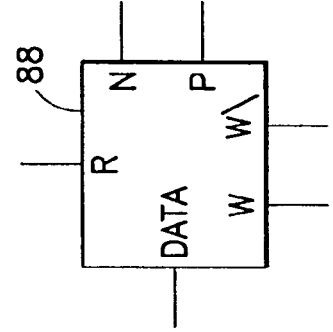

FIG. 22 shows a static latch 88 composed of two cross-coupled inverters 70 and 72, along with additional inverters 74 and 76 for read and write capability respectively. Programming of this latch is done by asserting the write line W, causing data to be stored on the input capacitance of the top inverter 70 in the cross-coupled pair. Data is read back on the DATA line by asserting the read line R, causing the tri-state output inverter 74 to drive the state of the DATA line to reflect the state of the latch. The outputs of the latch appear on the N and P lines and are fed to the switch control circuit as will be further described later. FIG. 23 shows an alternate embodiment using a dynamic latch. In this case, data is stored at the input capacitance of the inverter 78 when the write line W is asserted, thereby turning on the pass MOS-FET 80. The output of inverter 78 is inverted by inverter 82. Data is read back on the DATA line by asserting the read line R, which turns on the pass MOSFET 84. This type of latch is smaller than the circuit of FIG. 22, but has a limited period of time during which it retains data due to leakage currents. FIG. 24 shows how an extra inverter can be saved if one of the latch outputs is routed directly to an AND gate 86, as is the case in most of the architectures in this design. FIG. 25 is a high-level block diagram of the latch 88 showing its input and output signals. In both cases, transmission gates would be used in place of the pass MOSFETs, although using different supply voltages for the pass MOSFETs and the inverters could save the extra PMOS device.

It is understood that alternative devices such as DRAM or even other technologies could be used to implement the function of memory used here and these do not need to be discussed.

In one exemplary embodiment, the outputs N and P may be respectively sent to switching circuitry of the type described later with reference to FIG. 34, taken from the aforementioned U.S. patent application Ser. No. 10/248,968.

2) Multiplexed Address/Data Switch Cell with Future State Memory

Figure 26:
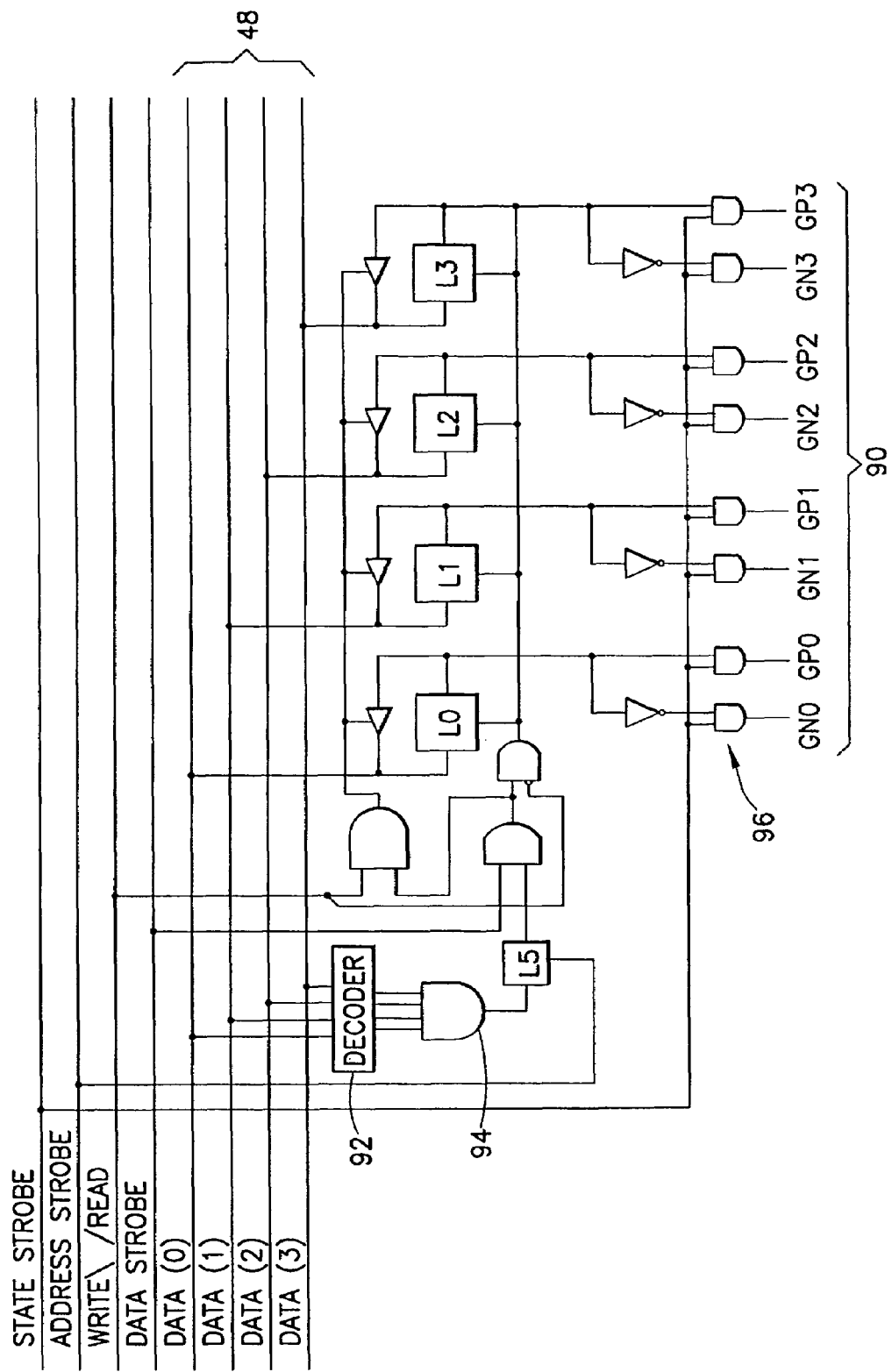
FIG. 26 is a drawing showing a unit switch cell with multiplexed address/data bus and future switch state memory in accordance with one embodiment of the invention.

In addition to the latches discussed above, each switch cell also contains addressing and control logic as shown in FIG. 26. The control logic comprises a plurality of AND gates 96, which output switch state control signals (referred to as "switch state control data" in the claims) GN0-GN3 and GP0-GP3 to the control gates of four analog switches (not shown) in a unit switch cell having one access switch and three matrix switches. For example, outputs GN0 and GP0 might control the on-off state of the access switch, while outputs GN1 and GP1 might control the on-off state of the first of the three matrix switches, and so forth.

FIG. 26 also shows digital control lines (i.e., STATE STROBE, ADDRESS STROBE, WRITE\READ, and DATA STROBE) and the multiplexed address/data bus 48. As shown, the bus 48 runs left to right across the array columns such that all of the other switch cells on this row (not shown) share the bus as well.

The address cycle begins by applying the address to the data bus. The address is received in the cell through the decoder block 92. This block consists of between zero and four inverters. Each decoder block implements the unique binary address of the particular column for the given cell. For example, the decoder for all cells in column 0 would contain no inverters; the decoder for column 1 would contain just one inverter; column 2, one inverter; column 3, two inverters; and so forth. The output of the decoder 92 is read by the AND gate 94. When ADDRESS STROBE is asserted, the AND gate output is stored in latch L5. Once the output of latch L5 is high, the cell is selected for the subsequent write operation. Note that this scheme enables broadcast writing if necessary. This feature is especially useful for updating subelements inside a ring that will all have every matrix switch turned on.

The write cycle begins by asserting WRITE\ to low. Data is then applied to the data bus and appears at the input of the future state latches (L0, L1, L2, L3). Programming of the latches occurs when DATA STROBE is asserted. Note that these latches do not immediately affect the state of the switches in the cell. This is an important feature since it makes possible quick transition between two different array configurations as would occur between transmit and receive.

Programming of the switch states is done by asserting STATE STROBE. This line enables the outputs of AND gates 96 to GN0-GN3 and GP0-GP3, which switch state control signals are output to the analog switch control gates (described in detail later with reference to FIG. 34). Since the switches themselves contain memory, it is possible to program both the current switch state and the next switch state. This requires two write operations. Once the first write is completed, STATE STROBE is asserted transferring the latch states to the switches. Then another write cycle to the same cell is used to set the future switch state onto the switch latches L0 through L3. Quick reconfiguration between transmit and receive is later done by asserting STATE STROBE, which transfers the data from the future state latches to the switch memory. To initiate a read operation for testing of the cell, an address cycle is done. This is followed by the read cycle which requires the WRITE\READ line to be asserted high.

Figure 27:
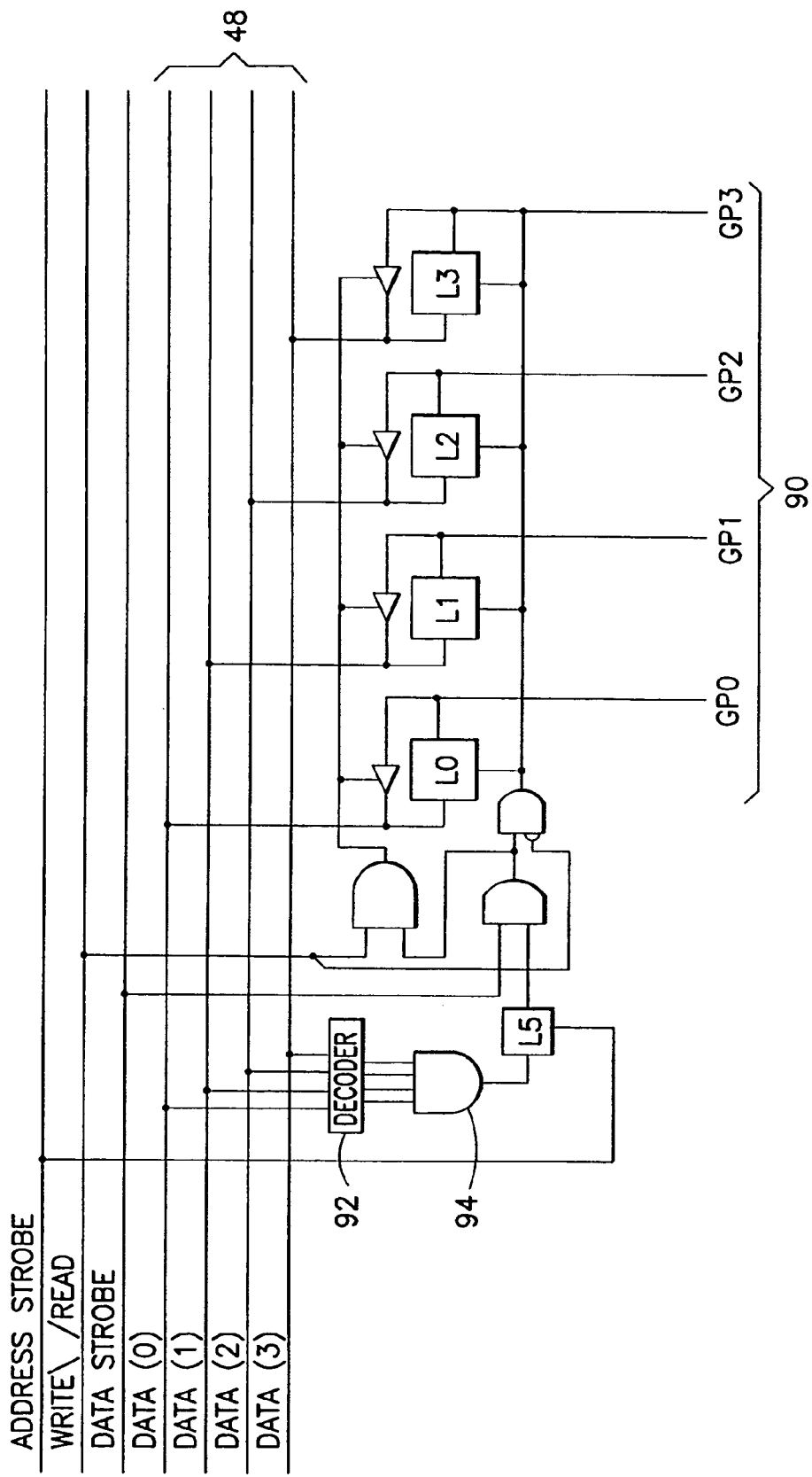
FIG. 27 is a drawing showing an alternative embodiment of the unit switch cell shown in FIG. 26 with data read incorporated in the latches.

FIG. 27 shows circuitry for interfacing to low-voltage switches wherein the outputs GN0-GN3 are not required.

3) Column-Addressed Switch Cell with Future State Memory

Figure 28:
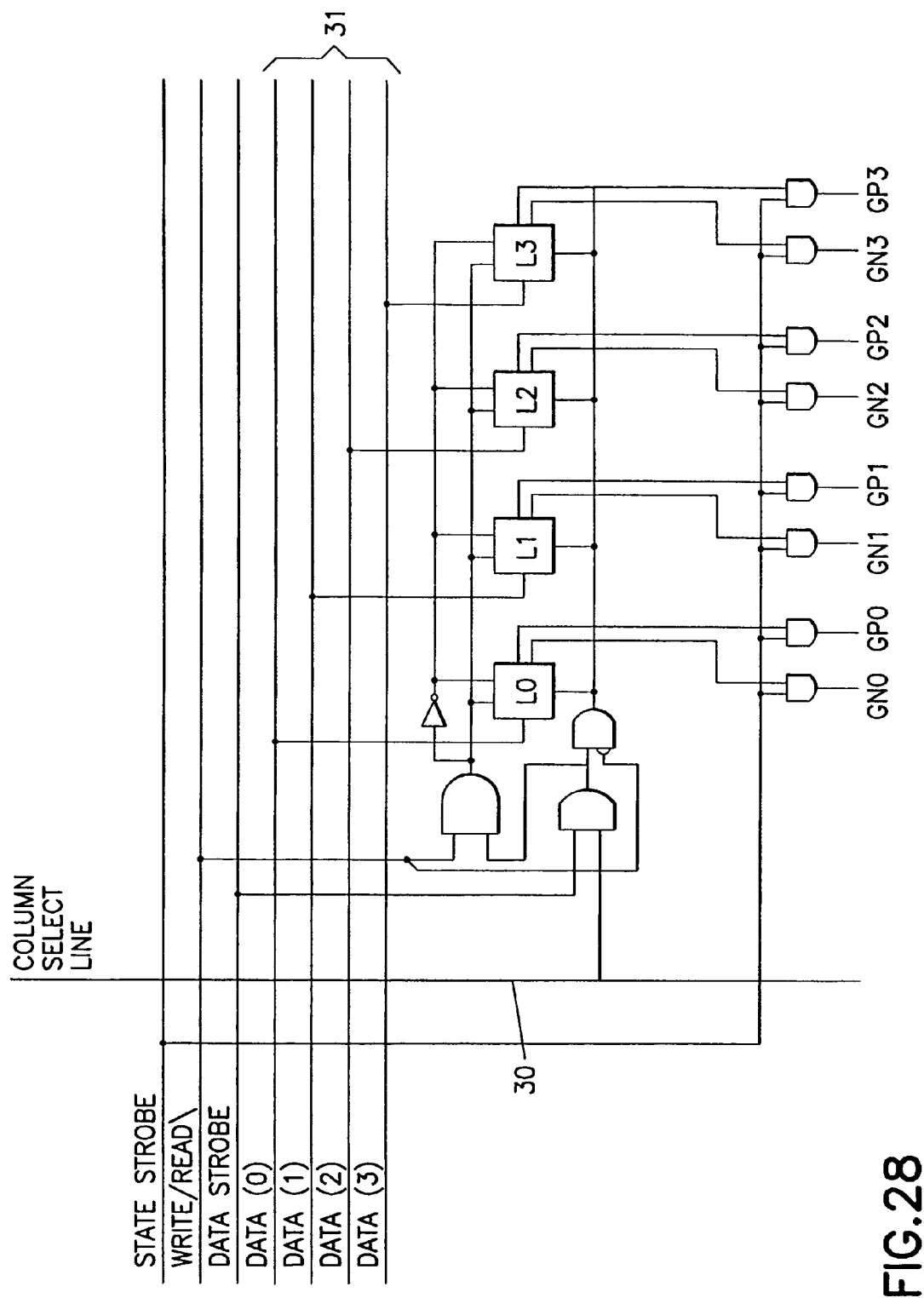
FIG. 28 is a drawing showing a unit switch cell with column addressing and future switch state memory in accordance with another embodiment of the invention.

FIG. 28 shows circuitry to implement a unit switch cell for the column-addressed scanning architecture. In this case, the addressing circuitry has been replaced by a single select line 30 that is asserted by the address generator (38 in FIG. 13). This select line is common to all cells in a given column. Operation of the cell is similar to that of the multiplexed cell with the exception that an address cycle is no longer required. As is evident from FIG. 28, this cell saves some circuitry over the multiplexed cell; however, as discussed previously, it is not as flexible.

4) Column-Addressed Switch Cell without Future State Memory

Figure 30:
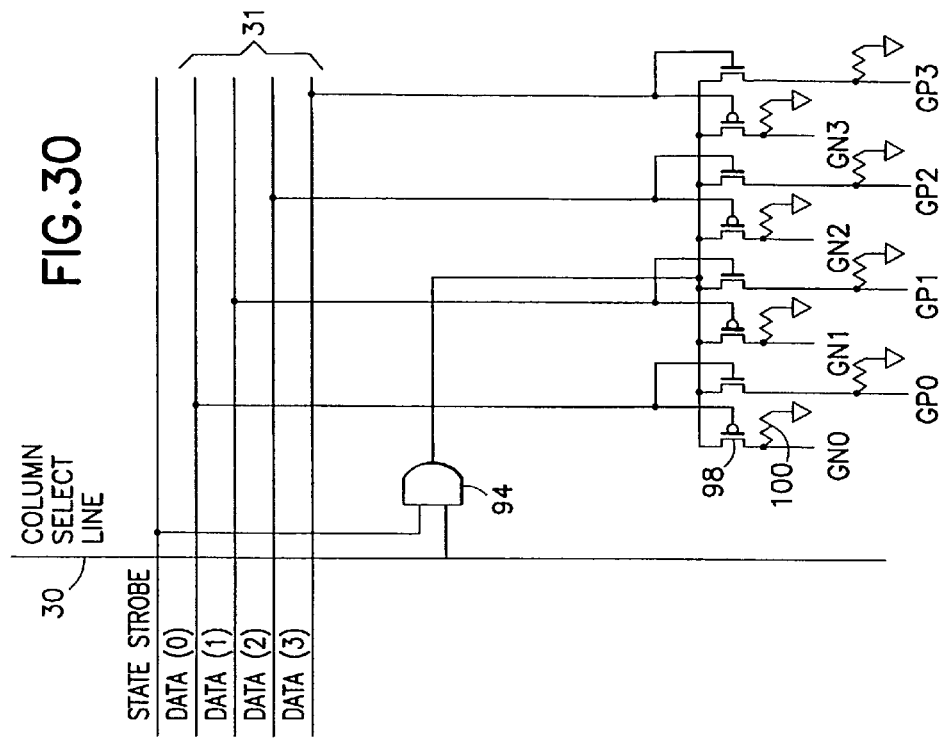
FIGS. 29 and 30 are drawings showing alternative embodiments of a unit switch cell with column addressing and without future switch state memory.
Figure 29:
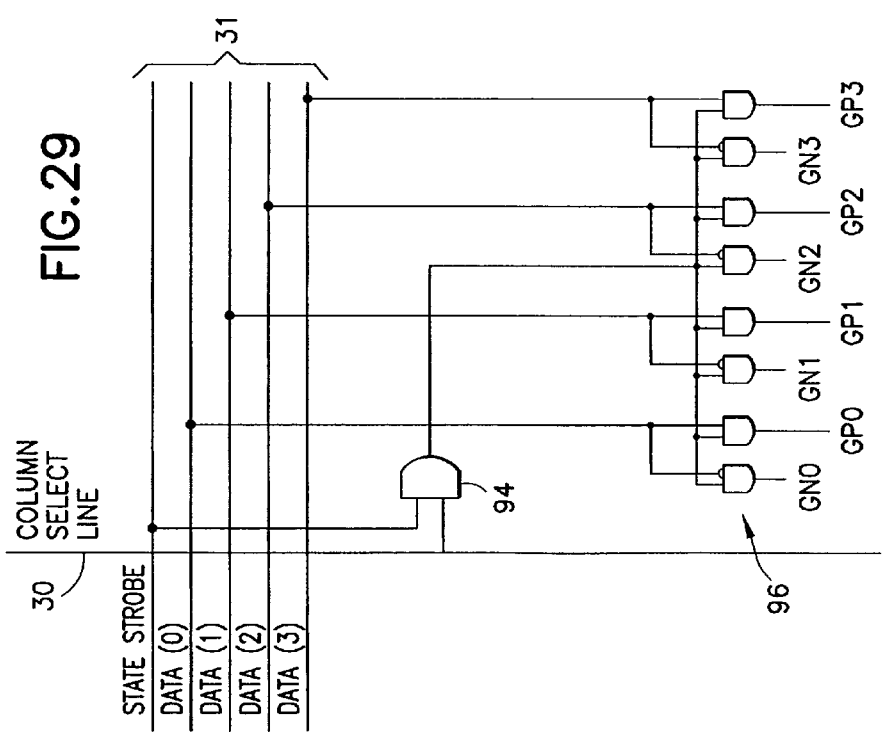

FIG. 29 shows circuitry to implement a unit switch cell with column addressing that does not have future state memory incorporated. This cell is the most compact of all of the possible cells; however, it is also the least flexible. As stated earlier, this cell would be very advantageous in a transducer that has very small acoustical subelements and so does not have enough area for more complex logic in each unit cell. FIG. 30 shows a preferred embodiment of this scheme which uses a respective MOSFET 98 and a respective resistor 100 in place of the each two-input AND gate and therefore is more compact than the circuit of FIG. 29.

5) Multiplexed Address/Data Switch Cell without Future State Memory

Figure 31:
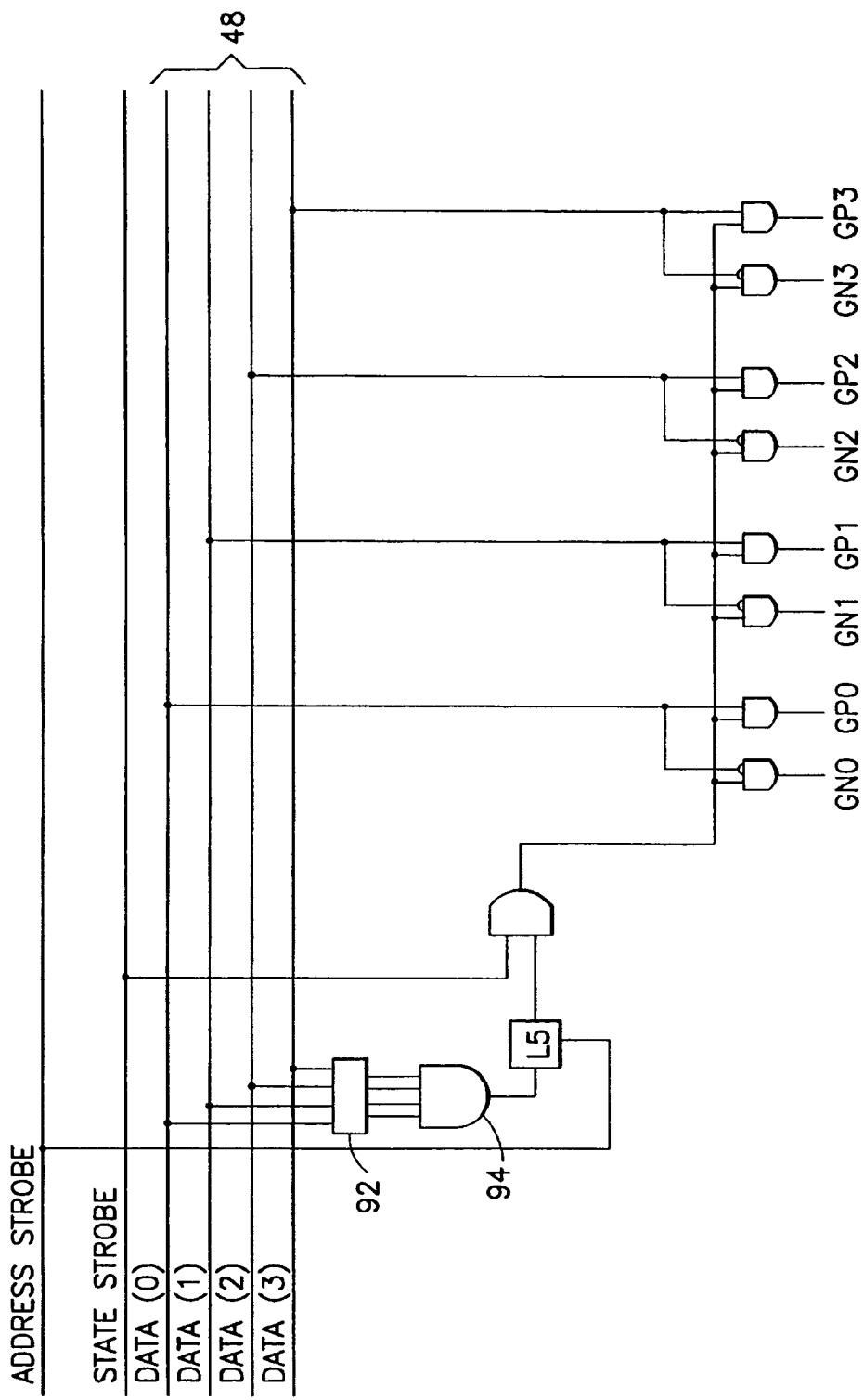
FIG. 31 is a drawing showing a unit switch cell with multiplexed address/data bus and without future switch state memory.

FIG. 31 shows circuitry to implement a unit switch cell with multiplexed data/address lines 48 that does not have future state memory. As with the previous cell type, this cell requires less space. It is more flexible in terms of addressing capability; however, it does not retain the ability to switch quickly between array patterns.

6) Shift Register Capable Cells

All of the cells with built-in latches described to this point do not explicitly show shift register capability. However with slight modifications, this capability can be added. This can be understood by examining FIG. 22 once more. By adding a FET switch between the output N and the DATA input of another adjacent cell, a two-bit shift register is created. Depending on the type of latch, some internal modifications may be necessary to create master/slave operation in order to implement the shift register functionality. This modification can be used to create very long shift registers by adding a switch to each cell along with the necessary control lines to enable shifting. The addition of these switches does not remove the programmability that is inherent in the cells discussed to this point. It instead creates a hybrid cell that has the best features of both architectures available.

Figure 32:
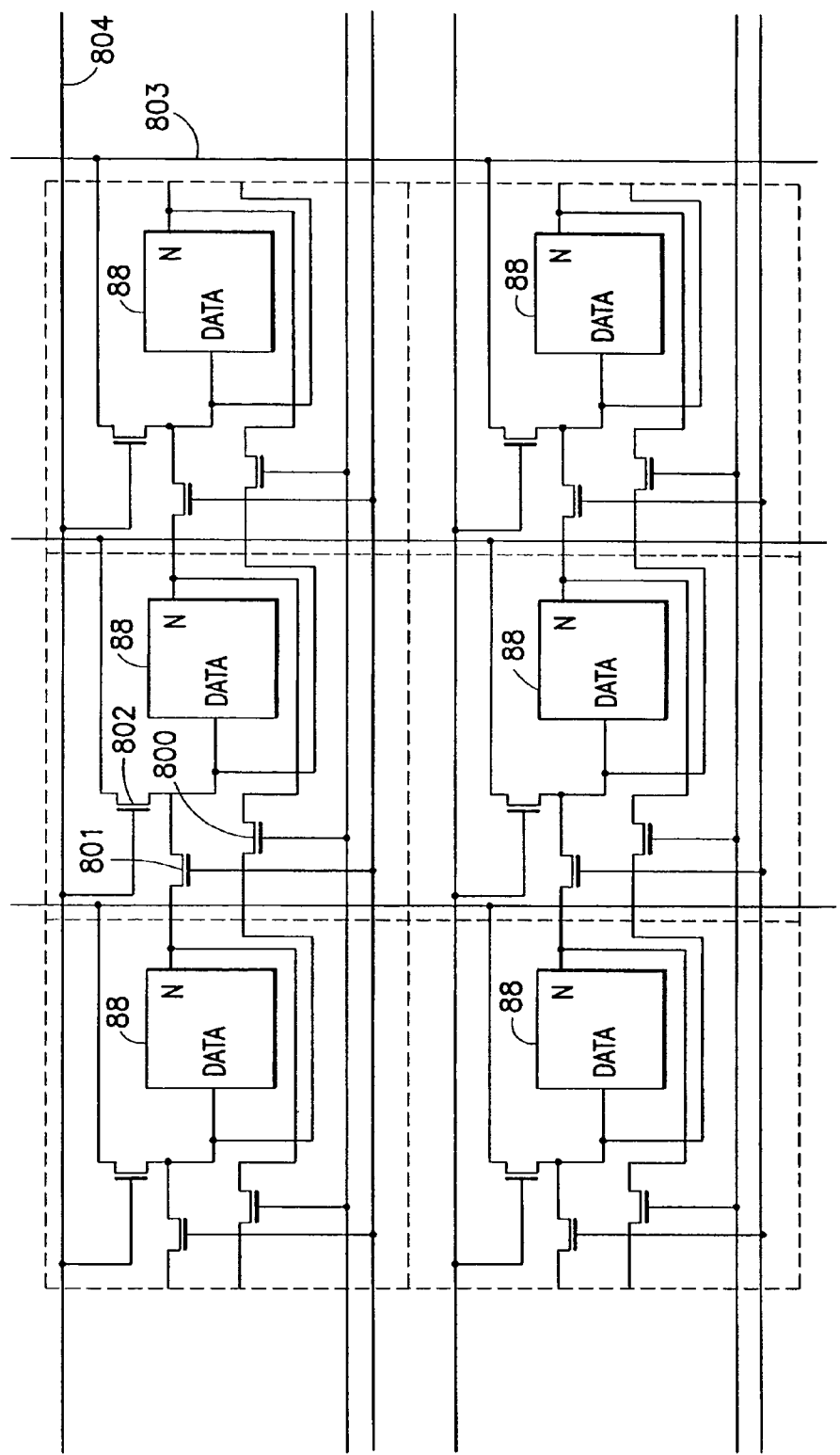
FIG. 32 is a drawing showing unit switch cells with bidirectional shift capability in the X direction.

FIG. 32 shows an array of six such cells in which each cell has bidirectional horizontal digital shift capability. It works as follows: Taking the top left shift register cell 88, the output N can be passed through right shift switch 801 to the shift register on the right. This accomplishes shift to the right when switch 801 is turned on. Similarly shift to the left can be accomplished by turning on left shift switch 800. Finally, for directly programming data into a given register 88, the register programming cell 802 can be turned on using data control line 804. This causes the external input programming data on the data bus line 803 to be transferred to the Data input of the register cell.

Figure 33:
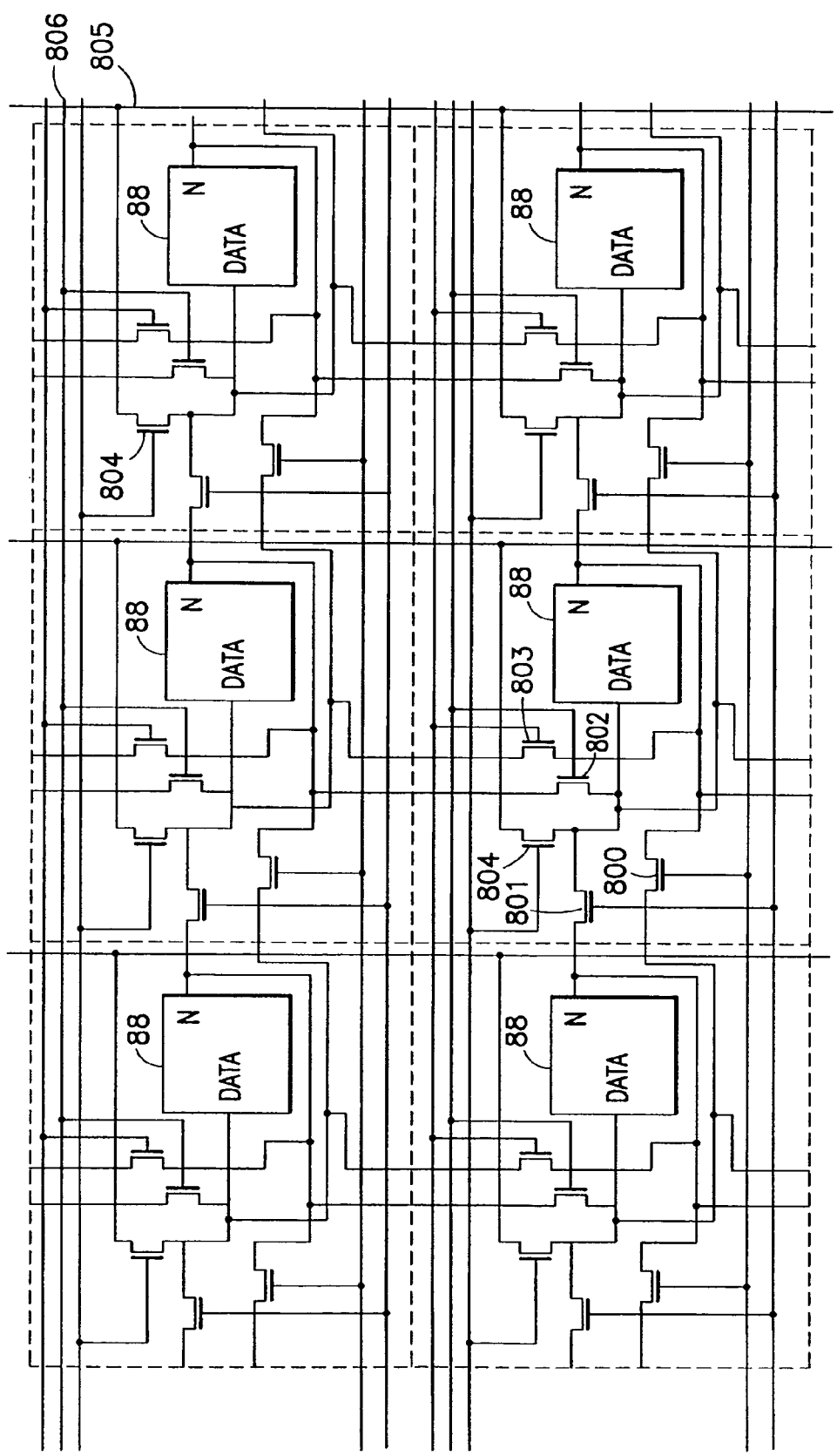
FIG. 33 is a drawing showing unit switch cells with bidirectional shift capability in the X and Y directions.

FIG. 33 shows the same array modified to be capable of bidirectional horizontal and vertical digital shift capability. It works as follows: Taking the bottom left shift register cell 88, the output N can be passed through right shift switch 801 to the shift register on the right. This accomplishes shift to the right when switch 801 is turned on. Similarly shift to the left can be accomplished by turning on left shift switch 800. Similarly, shift up and down can be accomplished using shift switches 803 and 802 respectively. Finally, for directly programming data into a given register 88, the register programming switch 804 can be turned on using data control line 806. This causes the external input programming data on the data bus line 805 to be transferred to the Data input of the register cell.

The additional switches in the arrays shown in FIGS. 32 and 33 represent an incremental increase in logic area and control complexity, but the added features of low-power operation and reduced programming time will justify this cost in many applications.

It is sometimes advantageous to be able to change the aperture along a scan line to create multiple transmit or receive focal points. Ordinarily, the switch configurations for these different apertures would have to be programmed into the array during imaging each time that a new aperture needs to be formed. Programming data from an external source has the following disadvantages: Increased power consumption to drive off-chip parasitic capacitances during multiple write cycles; reduced speed of operation due to the limitation of write speed from off-chip sources; and most importantly, increased digital noise during receive imaging. The latter can be especially problematic when imaging multiple focal zones deep into the body since maximum receive signal gain is applied to amplify the very small echoes that return from this depth. It is possible for the digital data transfer to generate noise fluctuations on the power lines and ground lines which would couple directly into the receive amplifiers and drown out the actual signals.

Figure 39:
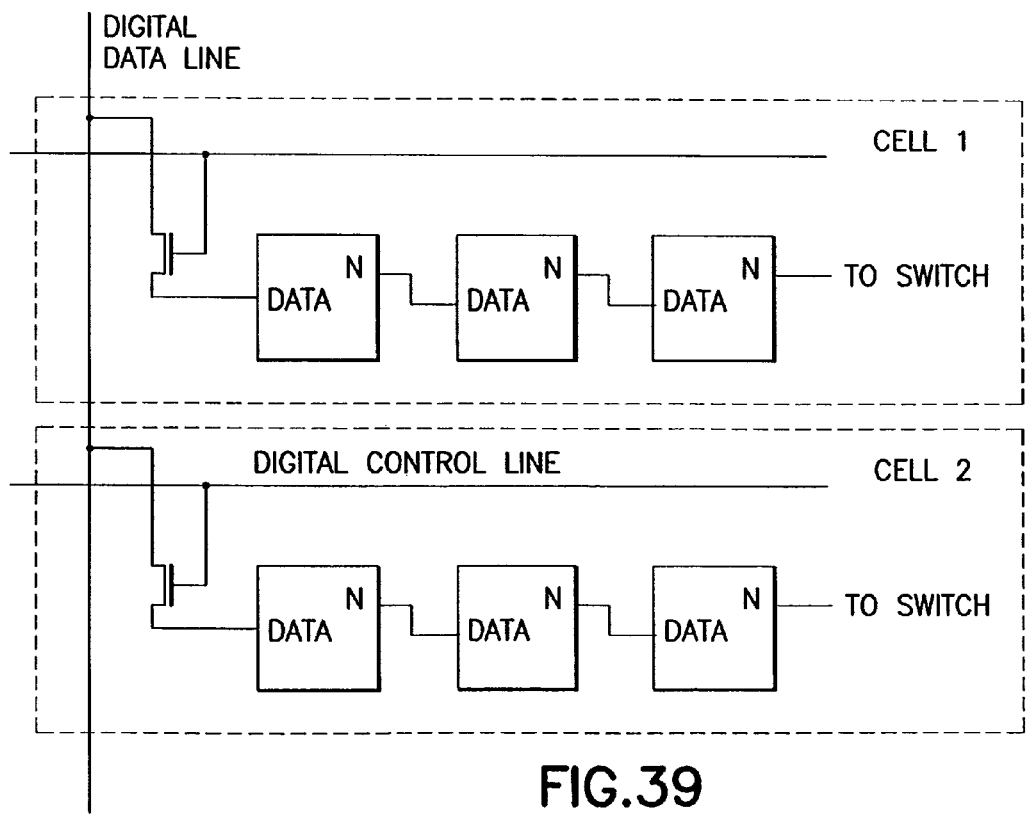
FIG. 39 is a drawing showing individual cells that can store data for switch settings for multiple apertures.

A solution to this problem is illustrated in FIG. 39. It is possible to provide individual cells that can store data for switch settings for multiple apertures as shown. A series of shift register elements (here only three are shown in each cell) is used to store multiple transmit or receive aperture switch configuration settings. For example, as shown in FIG. 39, three shift registers could be used to store three aperture switch settings for three receive focal zones. These registers would be programmed during the initial array programming cycle. During operation, the data would be successively shifted out to the switch control circuit for each aperture as needed. The advantage of this architecture is that the data is being shifted internal to the chip, where parasitic capacitances are much lower and therefore power expenditure and noise are reduced. In addition, the low parasitic capacitances allow the data transfer to take place at a much faster rate. Finally, since the data is already located in each cell, it can be shifted out in parallel, with Cell1 operating simultaneous to Cell2. This process can increase programming speed by the number of rows of cells in the array, which can be 100 or more times faster than bringing the data in from off-chip sources.

Depending on the fabrication process used, it may also be possible to increase the number of register bits much beyond the few shown here. In fact, in a process with co-integrated DRAM it can be possible to store all of the needed aperture settings for all aspects of operation locally within the array. As discussed before, this will provide great advantages in terms of power reduction, speed increases, and noise reduction, at the expense of use of more area on chip. Further, in a process that supports co-integrated EEPROM, it would be possible to program the data once into the probe and then never have to reprogram it again.

The various embodiments of the invention disclosed herein provide one or more of the following advantages: 1) fast configuration of arbitrary aperture patterns from one view to the next; 2) efficient programming of switch cells to minimize time and power requirements (e.g., by configuring only those switches that need to be changed from one view to the next); 3) the ability to translate aperture patterns quickly from view to view along the matrix axes while using minimum power; 4) the ability to change aperture configurations quickly between transmit and receive operations; 5) the ability to have multiple transmit/receive zones moving in different directions simultaneously; 6) programming of both transmit and receive switching configurations into the array); 7) definition of a region of interest that can be shifted along either or both array axes; 8) efficient scaling of architecture to large tiled arrays in view of: i) power constraints; ii) timing constraints; iii) retaining flexibility; and iv) minimizing complexity of configuration; 9) robustness to semiconductor defects; and 10) a fully programmable configuration of the switch matrix.

The general scanning architecture disclosed herein has application in ultrasound imaging systems comprising an array of acoustical subelements and a distributed switch matrix for interconnecting acoustical subelements to form larger acoustical elements and in other types of systems comprising an array of sensor elements that can be interconnected to former larger sensor elements by means of a distributed switching matrix.

Figure 34:
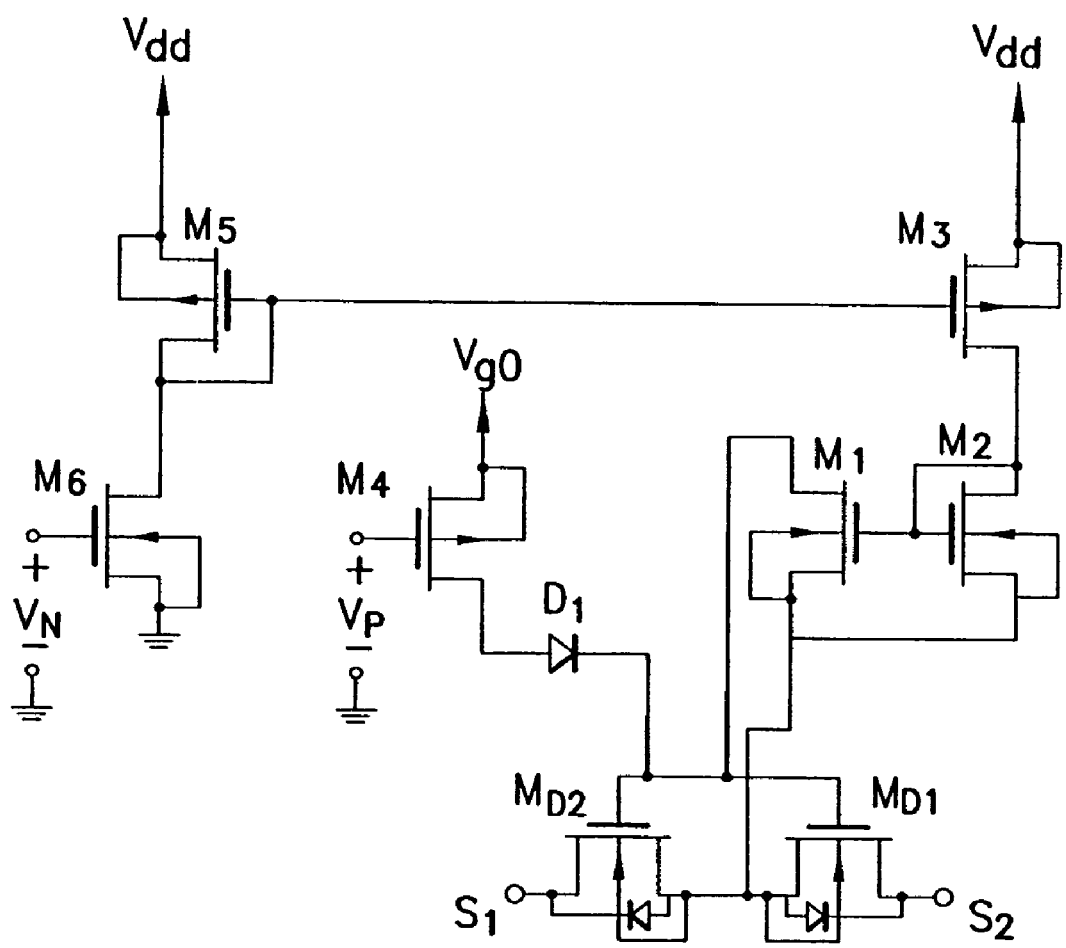
FIG. 34 is a drawing showing a high-voltage switching circuit disclosed in U.S. patent application Ser. No. 10/248,968.

The access and matrix switches of the distributed switching matrix may be the type of switch shown in FIG. 34. Transistors $M_{D1}$ and $M_{D2}$ are DMOS FETs that are connected back to back (source nodes shorted together) to allow for bipolar operation. This connection is necessary due to the parasitic body diodes (as shown in the schematic) that would otherwise provide a conduction path from drain to source of either device during the positive or negative phase of the ultrasound transmit pulse. Current flows through the switch terminals $S_1$ and $S_2$ whenever both $M_{D1}$ and $M_{D2}$ are turned on. To turn on the switch, the gate voltage of these devices must be greater than their source voltage by a threshold voltage. Above the threshold voltage, switch ON resistance varies inversely with the gate voltage. Since the source voltage will be close to the drain voltage (for low ON resistance and low current), the source voltage will track the ultrasound transmit pulse voltage. In order for the gate-source voltage to remain constant, the gate voltage must also track the transmit pulse voltage. This can be achieved by isolating the source and gate from the switch control circuitry and providing a fixed potential at the gate with reference to the source. In the embodiment shown in FIG. 34, a dynamic level shifter is used. This level shifter operates as follows:

Transistor $M_4$ is a high-voltage PMOS transistor capable of withstanding the process maximum (e.g., 100 V) between its drain and source terminals. The source of transistor $M_4$ is biased at the global switch gate bias voltage $V_{g0}$ (nominally 5 V) as shown. In order to turn on the switch, the gate voltage $V_P$ of transistor $M_4$ is transitioned from high (5 V) to low (0 V), causing the global bias voltage $V_{g0}$ to be applied through transistor $M_4$ to the shared gate terminal of the FETs $M_{D1}$ and $M_{D2}$. The diode $D_1$ is provided to prevent transistor $M_4$ from turning on when the DMOS switch gate voltage drifts above $V_{g0}$. Once the switch gate voltage has reached $V_{g0}$, the parasitic gate capacitance of the FETs $M_{D1}$ and $M_{D2}$ will retain this voltage. For this reason, once the gate voltage has stabilized, transistor $M_4$ can be turned off to conserve power. Leakage current at the drain of transistor $M_4$ will eventually dissipate the bias voltage at the switch gate, but this voltage can be reprogrammed periodically if necessary. The fact that the switch ON state is effectively stored on the switch gate capacitance means that the switch has its own memory, which is useful since extra state flip-flops do not need to be provided for that purpose.

When in the ON state, the switch can be turned off using gate clamp NMOS transistor $M_1$. This is done by applying a turn-on voltage to the gate of transistor $M_1$ using the level shifter composed of transistors $M_2$, $M_3$, $M_5$ and $M_6$. When this transistor is turned on, it forces the switch gate voltage to be equal to the switch source voltage, which moves the switch $M_{D1}$ and $M_{D2}$ to its OFF state. The action of making these voltages equal effectively dissipates the charge left on the gate capacitance after the turn-on operation described above. Once the charge is removed, transistor M, does not have to be left on. This means that the control level shifter circuit for this device can be turned off once the switch has stabilized, and this will save power. Again, the OFF state can be stored for an extended period and reprogrammed if necessary.

The circuit shown in FIG. 34 has the following advantages: (1) low power since there is no static current dissipation to keep the device in the ON or OFF state; power is only dissipated during transition from one state to the next state; (2) state memory since the switch state is effectively stored on the switch gate capacitance; (3) cascadable switches due to the absence of a static bias current and voltage drop in the ON state; and (4) programmable ON resistance since $V_{g0}$ can be individually controlled.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

The invention claimed is:

1. A device comprising:
   a multiplicity of sensors arranged along generally parallel lines;
   a multiplicity of bus lines,
   a first multiplicity of switches for selectively electrically connecting sensors to bus lines, wherein each switch of said first multiplicity is of a type that can memorize data representing its current switch state, each sensor having at least a respective switch of said first multiplicity associated therewith;
   a second multiplicity of switches for selectively electrically connecting sensors to each other, wherein each switch of said second multiplicity is of a type that can memorize data representing its current switch state, each sensor having at least a respective switch of said second multiplicity associated therewith;
   data generator circuitry for generating switch state data representing the state of switches of said first and second multiplicities to be programmed;
   address generator circuitry for generating address data identifying said switches of said first and second multiplicities to be programmed; and
   a multiplicity of control logic circuits for outputting switch state control data to said switches of said first and second multiplicities to be programmed in response to receipt of said switch state data, each sensor having a respective control logic circuit associated therewith, said switch state control data controlling the state of said switches and being derived from said switch state data, and each sensor having a respective control logic circuit associated therewith.

2. The device as recited in claim 1, wherein each of said sensors comprises a respective ultrasonic transducer subelement.

3. The device as recited in claim 2, wherein each of said ultrasonic transducer subelements comprises a respective plurality of cMUT cells that are not switchably disconnectable from each other.

4. The device as recited in claim 2, wherein said ultrasonic transducer subelements are arranged in a hexagonal array, each ultrasonic transducer subelement having three switches of said second multiplicity associated therewith for respectively electrically connecting an ultrasonic transducer element with any of three neighboring ultrasonic transducer subelements.

5. The device as recited in claim 1, further comprising a view generator that programs said address and data generator circuitry to configure the first and second multiplicities of switches as required for a given view.

6. The device as recited in claim 1, further comprising a multiplicity of latches for storing said switch state data from said data generator circuitry during a first time period and then writing said switch state data into said control logic circuits during a second time period subsequent to said first time period.

7. The device as recited in claim 6, wherein said switch state control data memorized in said selected switches of said first and second multiplicities of switches represents a transmit aperture pattern, while said switch state data stored in said latches will be converted into switch state control data that represents a receive aperture pattern.

8. The device as recited in claim 1, wherein the switches identified during one cycle represent a first region of interest, while the switches identified during a subsequent cycle represent a second region of interest, but said second region of interest being shifted relative to said first region of interest.

9. The device as recited in claim 1, wherein the switch state control data memorized in a first set of switches of said first and second multiplicities during a predetermined time period represents a transmit aperture pattern, while the switch state control data memorized in a second set of switches of said first and second multiplicities during said predetermined time period represents a receive aperture pattern.

10. The device as recited in claim 1, further comprising a multiplicity of address/data bus lines for carrying said address data and said switch state data, and a multiplicity of multiplexers situated between said data and address generator circuitry and said address/data bus lines, said multiplexers connecting said address generator circuitry to said address/data bus lines in a first multiplexer state and connecting said data generator circuitry to said address/data bus lines in a second multiplexer state.

11. The device as recited in claim 6, further comprising:
means for connecting respective sets of said latches along an X direction to form respective X-direction shift registers;
a multiplicity of address/data bus lines respectively connected to said sets of latches;
a multiplicity of multiplexers situated between said data and address generator circuitry and said sets of address/data buses, said multiplexers connecting said address generator circuitry to said address/data buses in a first multiplexer state and connecting said data generator circuitry to said address/data buses in a second multiplexer state; and
X control means for controlling the shifting of switch state data in an X direction in selected latches.

12. The device as recited in claim 11, further comprising:
means for connecting respective sets of said latches along a Y direction to form respective Y-direction shift registers; and
Y control means for controlling the shifting of switch state data in a Y direction in selected latches.

13. The device as recited in claim 11, wherein the address data and the switch state data are selected to repair shift register lines that have inoperable elements.

14. The device as recited in claim 11, wherein selected latches are programmed by said address and data generator circuitry for a region of interest, and thereafter the switch state data in said selected latches is shifted by said X control means for shifting said region of interest.

15. The device as recited in claim 1, further comprising a multiplicity of data bus lines for electrically connecting said data generator circuitry to said control logic circuitry, and a multiplicity of column select lines for electrically connecting said address generator circuitry to said control logic circuitry, said multiplicity of data bus lines running generally parallel to said lines of sensors, and said column select lines being not parallel to said data bus lines.

16. The device as recited in claim 15, wherein said address generator circuitry comprises a first shift register loaded with a region of interest bit pattern that is shifted to move the block of columns that accept the switch state data from said data generator circuitry.

17. The device as recited in claim 16, wherein said address generator circuitry further comprises a second shift register that shifts a bit in round robin within the bounds of said region of interest to select columns in sequence for addressing.

18. The device as recited in claim 1, further comprising a multiplicity of address/data bus lines for carrying said address data and said switch state data from said address and data generator circuitry respectively, and a multiplicity of latches situated between said data and address generator circuitry and said address/data bus lines, one latch per address/bus line.

19. The device as recited in claim 1, wherein said data generator circuitry comprises a dedicated data generator for each line of sensors.

20. The device as recited in claim 1, wherein said data generator circuitry comprises an FPGA, a CPU or a digital ASIC which generates data algorithmically.

21. The device as recited in claim 1, wherein said data generator circuitry comprises a RAM, ROM, EPROM, EEPROM, MRAM, FRAM, or any other memory device for storing said switch state data coupled to an FPGA, CPU, or ASIC to direct readout of switch state data to the array.

22. The device as recited in claim 1, wherein said address generator circuitry and said data generator circuitry are respectively provided on both sides of said multiplicity of sensors and the switches of said first and second multiplicities associated with said lines of sensors are divided into right and left segments, the switches of said left segments being controlled by said address and data generator circuitry on one side, and the switches of said right segments being controlled by said address and data generator circuitry on the other side.

23. The device as recited in claim 15, wherein said address generator circuitry is provided above and below said multiplicity of sensors and the column select lines are divided into top and bottom segments, the switches of said first and second multiplicities connected to said top segments of said column select lines being addressed by said address generator circuitry on the top, and the switches of said first and second multiplicities connected to said bottom segments of said column select lines being addressed by said address generator circuitry on the bottom.

24. The device as recited in claim 1, further comprising a multiplicity of decoding circuits for decoding address data from said address generator circuitry, each sensor being associated with a respective decoding circuit.

25. The device as recited in claim 1, wherein each control logic circuit comprises a respective plurality of logic gates that output said switch state control data in response to a global strobe signal.

26. The device as recited in claim 6, further comprising a multiplicity of address/data bus lines for carrying said address data and said switch state data from said address and data generator circuitry respectively, wherein each of said latches is of a type wherein the switch state data stored therein can be read out to said address/data bus lines in response to a read command.

27. A device comprising:
a multiplicity of sensors arranged along generally parallel lines;
a multiplicity of bus lines, and
a multiplicity of unit switch cells, each unit switch cell being associated with a respective sensor and comprising: (a) a first switch for connecting said associated sensor to a bus line, (b) a second switch for connecting said associated sensor to a neighboring sensor, and (c) a control logic circuit for outputting switch state control data to said first and second switches in response to receipt of switch state data representing the desired states of said first and second switches, said switch state control data controlling the state of said first and second switches and being derived from said switch state data, and each of said first and second switches being of a type that can memorize data representing its current switch state;
data generator circuitry for generating switch state data for selected first and second switches; and
address generator circuitry for generating address data identifying which of said first and second switches have been selected to be programmed.

28. The device as recited in claim 27, wherein each of said sensors comprises a respective ultrasonic transducer subelement.

29. The device as recited in claim 27, wherein each of said unit switch cells further comprises respective first and second latches for storing switch state data for said first and second switches during a first time period and then writing said switch state data into said control logic circuit during a second time period subsequent to said first time period.

30. The device as recited in claim 27, wherein each of said unit switch cells further comprises a decoding circuit for decoding address data from said address generator circuitry.

31. The device as recited in claim 29, wherein the first and second latches for unit switch cells associated with a line of sensors are connected to form a shift register.

32. The device as recited in claim 27, wherein each of said unit switch cells comprises means for storing multiple transmit or receive aperture switch settings locally within each cell and reading out the respective switch settings during transmit or receive beam formation to create multiple transmit or receive focal zones.

33. The device as recited in claim 32, wherein said storing means comprise more than one register for storage of multiple switch settings that can be read out during transmit or receive imaging.

34. The device as recited in claim 33, wherein said registers form a shift register with serial data read-out.

35. The device as recited in claim 33, wherein said registers form a random access memory with data read out selectively using random access.

36. A device comprising:
a multiplicity of sensors arranged along generally parallel lines;
a multiplicity of bus lines,
a first multiplicity of switches for selectively electrically connecting sensors to bus lines, wherein each switch of said first multiplicity is of a type that can memorize data representing its current switch state, each sensor having at least a respective switch of said first multiplicity associated therewith;
a second multiplicity of switches for selectively electrically connecting sensors to each other, wherein each switch of said second multiplicity is of a type that can memorize data representing its current switch state, each sensor having at least a respective switch of said second multiplicity associated therewith;
data generator circuitry for generating switch state data representing the state of switches of said first and second multiplicities to be programmed;
a multiplicity of latches for storing said switch state data from said data generator circuitry;
a multiplicity of data bus lines respectively connected to said sets of latches;
means for connecting respective sets of said latches along an X direction to form respective X-direction shift registers;
Y control means for controlling the shifting of switch state data in an Y direction in selected latches;
means for connecting respective sets of said latches along a Y direction to form respective Y-direction shift registers; and
X control means for controlling the starting point at which switch state data enters said sets of latches and controlling the shifting of switch state data in a X direction in selected latches.

37. A reconfigurable sensor array comprising:
(a) a multiplicity of sensors tiled over a two-dimensional area;
(b) a multiplicity of bus lines;
(c) a multiplicity of switches for connecting selected sensors to each other or connecting selected sensors to respective bus lines, wherein each of said switches comprises respective switch state memory, said switch state memories storing switch state control data representing the current states of said switches;
(d) a multiplicity of latches for storing switch state data representing the future states of said switches; and
(e) control logic for overwriting said switch state control data in the switch state memories of said switches with new switch state control data derived from said switch state data output from said latches.

38. The sensor array as recited in claim 37, wherein each of said sensors comprises a respective ultrasonic transducer subelement.

39. The sensor array as recited in claim 38, wherein each of said ultrasonic transducer subelements comprises a respective plurality of cMUT cells that are not switchably disconnectable from each other.

40. The sensor array as recited in claim 37, further comprising data generator circuitry for generating said switch state data and a multiplicity of data lines for carrying said switch state data from said data generator circuitry toward said latches.

41. The sensor array as recited in claim 40, further comprising address generator circuitry for generating address data that identifies selected switches to be programmed based on said switch state data.

42. The sensor array as recited in claim 41, wherein each of said components (a) through (e) are integrated into a substrate or lamination, while said data and address generator circuitry are not integrated into said substrate or lamination.

43. The device as recited in claim 11, wherein said X control means comprises first and second region of interest shifting controllers.

* * * * *